(12) United States Patent
Assell et al.

(10) Patent No.: US 10,271,859 B2
(45) Date of Patent: Apr. 30, 2019

(54) UNDERCUTTING SYSTEM FOR USE IN CONJUNCTION WITH SACROILIAC FUSION

(71) Applicant: RTI Surgical, Inc., Alachua, FL (US)

(72) Inventors: Robert Assell, St. Paul, MN (US); Jeremy Carr, Lauderdale, MN (US); Eugene Dickhudt, Lino Lakes, MN (US); Thomas Berg, Centerville, MN (US); Brian Beaubien, St. Paul, MN (US)

(73) Assignee: RTI Surgical, Inc., Alachua, FL (US)

( * ) Notice: Subject to any disclaimer, the term of this patent is extended or adjusted under 35 U.S.C. 154(b) by 0 days.

(21) Appl. No.: 15/865,592

(22) Filed: Jan. 9, 2018

(65) Prior Publication Data

US 2018/0221033 A1      Aug. 9, 2018

Related U.S. Application Data

(62) Division of application No. 14/593,579, filed on Jan. 9, 2015, now Pat. No. 9,861,375.

(60) Provisional application No. 61/925,280, filed on Jan. 9, 2014.

(51) Int. Cl.
*A61B 17/16*      (2006.01)
(52) U.S. Cl.
CPC ........ *A61B 17/1671* (2013.01); *A61B 17/162* (2013.01); *A61B 17/1615* (2013.01); *A61B 17/1617* (2013.01); *A61B 2017/1602* (2013.01)

(58) Field of Classification Search
CPC . A61B 17/16; A61B 17/1628; A61B 17/1631; A61B 17/1633; A61B 17/1659; A61B 17/1662; A61B 17/1664; A61B 17/1671
See application file for complete search history.

(56) References Cited

U.S. PATENT DOCUMENTS

| 5,015,255 A | 5/1991 | Kuslich |
| 5,242,444 A | 9/1993 | MacMillian |
| 5,334,205 A | 8/1994 | Cain |
| 5,591,170 A | 1/1997 | Spievack |
| 5,925,056 A | 7/1999 | Thomas |

(Continued)

FOREIGN PATENT DOCUMENTS

| DE | 202009006906 | 7/2009 |
| EP | 0369603 | 5/1990 |

(Continued)

OTHER PUBLICATIONS

Article 94(3) EPC from European Patent Application No. 10798691.1 dated Jul. 6, 2017; 11 pages.

(Continued)

*Primary Examiner* — Eric S Gibson
(74) *Attorney, Agent, or Firm* — Fitch, Even, Tabin & Flannery LLP

(57) ABSTRACT

A method of preparing a region between adjacent bones for fusion. A first aperture is formed that extends through one of the bones. An undercutting system is inserted into the first aperture. The undercutting system includes an insertion apparatus and a cutting assembly. A first path is cut between the adjacent bones by extending or retracting the cutting assembly with respect to the insertion apparatus.

6 Claims, 12 Drawing Sheets

(56) References Cited

U.S. PATENT DOCUMENTS

| | | |
|---|---|---|
| 5,928,239 A | 7/1999 | Mirza |
| 6,358,251 B1 | 3/2002 | Mirza |
| 6,440,138 B1 | 8/2002 | Reiley |
| 6,635,059 B2 | 10/2003 | Randall |
| 6,679,886 B2 | 1/2004 | Weikel |
| 6,726,690 B2 | 4/2004 | Eckman |
| 6,740,090 B1 | 5/2004 | Cragg |
| 6,746,451 B2 * | 6/2004 | Middleton ......... A61B 17/1617 606/180 |
| 6,821,276 B2 | 11/2004 | Lambrecht |
| 6,923,813 B2 | 8/2005 | Phillips |
| 6,939,351 B2 | 9/2005 | Eckman |
| D601,711 S | 10/2009 | Lin |
| 7,699,849 B2 | 4/2010 | Eckman |
| 7,867,233 B2 | 1/2011 | Shaolian |
| 7,879,038 B2 | 2/2011 | Reiley |
| 7,909,827 B2 | 3/2011 | Reiley |
| 7,914,545 B2 | 3/2011 | Ek |
| 7,918,849 B2 * | 4/2011 | Bleich ................ A61B 17/1659 606/1 |
| 8,062,298 B2 * | 11/2011 | Schmitz ........... A61B 17/00234 606/79 |
| 8,109,957 B2 | 2/2012 | Stad |
| 8,114,084 B2 | 2/2012 | Betts |
| 8,192,436 B2 * | 6/2012 | Schmitz ............. A61B 17/1659 606/85 |
| 8,257,356 B2 * | 9/2012 | Bleich ................ A61B 17/1671 606/79 |
| 8,348,950 B2 * | 1/2013 | Assell ................ A61B 17/1617 606/79 |
| 8,398,640 B2 * | 3/2013 | Hawkins ........... A61B 17/1624 30/381 |
| 8,801,626 B2 * | 8/2014 | Sun ...................... A61B 5/4893 600/554 |
| 9,050,112 B2 | 6/2015 | Greenhalgh |
| 9,101,371 B2 * | 8/2015 | Assell ................ A61B 17/1617 |
| 9,113,919 B2 * | 8/2015 | Assell ................ A61B 17/1617 |
| 9,119,639 B2 * | 9/2015 | Kuntz ................ A61B 17/1642 |
| 9,149,283 B2 * | 10/2015 | Assell ............ A61B 17/320016 |
| 9,161,763 B2 * | 10/2015 | Assell ................ A61B 17/1617 |
| 9,204,896 B2 * | 12/2015 | Williams ........... A61B 17/1659 |
| 9,314,253 B2 * | 4/2016 | Mimran ............. A61B 17/1671 |
| 9,345,488 B2 * | 5/2016 | Assell ................ A61B 17/1617 |
| 9,610,083 B2 * | 4/2017 | Kuntz ................ A61B 17/1642 |
| 9,662,123 B2 * | 5/2017 | Tally ................. A61B 17/1671 |
| 9,662,124 B2 * | 5/2017 | Assell ................ A61B 17/1617 |
| 9,713,478 B2 * | 7/2017 | Assell ................... A61B 17/16 |
| 9,861,375 B2 | 1/2018 | Assell |
| 2001/0034526 A1 | 10/2001 | Kuslich |
| 2001/0049527 A1 | 12/2001 | Cragg |
| 2002/0183758 A1 | 12/2002 | Middleton |
| 2002/0193781 A1 * | 12/2002 | Loeb .................. A61B 18/1402 606/15 |
| 2003/0004517 A1 | 1/2003 | Anderson |
| 2003/0191474 A1 * | 10/2003 | Cragg ................ A61B 17/1671 606/79 |
| 2004/0092933 A1 | 5/2004 | Shaolian |
| 2004/0267269 A1 | 12/2004 | Middleton |
| 2005/0137600 A1 | 6/2005 | Jacobs |
| 2005/0137601 A1 | 6/2005 | Assell |
| 2005/0159746 A1 | 7/2005 | Grob |
| 2005/0203527 A1 | 9/2005 | Carrison |
| 2005/0261695 A1 | 11/2005 | Cragg |
| 2005/0267482 A1 | 12/2005 | Hyde |
| 2006/0089650 A1 * | 4/2006 | Nolde ................ A61B 17/1659 606/85 |
| 2006/0111780 A1 | 5/2006 | Peterson |
| 2006/0155289 A1 | 7/2006 | Windhager |
| 2007/0055260 A1 | 3/2007 | Cragg |
| 2007/0123889 A1 | 5/2007 | Malandain |
| 2007/0198020 A1 | 8/2007 | Reiley |
| 2007/0260252 A1 * | 11/2007 | Schmitz ............. A61B 17/1659 606/79 |
| 2007/0260270 A1 | 11/2007 | Assell |
| 2007/0265652 A1 | 11/2007 | Assell |
| 2008/0009861 A1 | 1/2008 | Stark |
| 2008/0009875 A1 | 1/2008 | Sankaran |
| 2008/0033465 A1 * | 2/2008 | Schmitz ............. A61B 17/1604 606/170 |
| 2008/0091199 A1 | 4/2008 | Cragg |
| 2008/0114364 A1 * | 5/2008 | Goldin ............... A61B 17/1617 606/79 |
| 2008/0114365 A1 | 5/2008 | Sasing |
| 2008/0269754 A1 | 10/2008 | Lutz |
| 2008/0287741 A1 * | 11/2008 | Ostrovsky .......... A61B 1/00071 600/141 |
| 2008/0294166 A1 | 11/2008 | Goldin |
| 2008/0294167 A1 | 11/2008 | Schumacher |
| 2008/0312660 A1 * | 12/2008 | Bleich .................. A61B 5/1076 606/102 |
| 2008/0319481 A1 | 12/2008 | Moore |
| 2009/0138053 A1 | 5/2009 | Assell |
| 2009/0149865 A1 * | 6/2009 | Schmitz ............. A61B 17/1659 606/114 |
| 2009/0216238 A1 | 8/2009 | Stark |
| 2009/0259261 A1 | 10/2009 | Reiley |
| 2009/0319043 A1 | 12/2009 | McDevitt |
| 2010/0004651 A1 | 1/2010 | Biyani |
| 2010/0016968 A1 | 1/2010 | Moore |
| 2010/0030216 A1 | 2/2010 | Arcenio |
| 2010/0131011 A1 | 5/2010 | Stark |
| 2010/0168747 A1 * | 7/2010 | Lynch ................ A61B 17/1668 606/79 |
| 2010/0241123 A1 | 9/2010 | Middleton |
| 2010/0274250 A1 * | 10/2010 | Wallace .............. A61B 17/025 606/79 |
| 2010/0331883 A1 * | 12/2010 | Schmitz ............. A61B 10/0275 606/249 |
| 2011/0028978 A1 | 2/2011 | Li |
| 2011/0060314 A1 * | 3/2011 | Wallace ............. A61B 17/1659 604/528 |
| 2011/0087294 A1 | 4/2011 | Reiley |
| 2011/0098709 A1 | 4/2011 | Malandain |
| 2011/0112539 A1 * | 5/2011 | Wallace ............. A61B 17/1671 606/79 |
| 2011/0118796 A1 | 5/2011 | Reiley |
| 2011/0160731 A1 * | 6/2011 | Bleich ................ A61B 17/1671 606/79 |
| 2011/0166575 A1 * | 7/2011 | Assell ................ A61B 17/1617 606/79 |
| 2011/0178523 A1 * | 7/2011 | Siegal ............ A61B 17/320016 606/79 |
| 2011/0184420 A1 | 7/2011 | Barnhouse |
| 2011/0264229 A1 | 10/2011 | Donner |
| 2011/0295272 A1 | 12/2011 | Assell |
| 2012/0022568 A1 | 1/2012 | Koblish |
| 2012/0078255 A1 * | 3/2012 | Bleich ................ A61B 17/1671 606/79 |
| 2012/0095468 A1 * | 4/2012 | Wallace .............. A61B 17/025 606/79 |
| 2012/0323285 A1 | 12/2012 | Assell |
| 2012/0330314 A1 * | 12/2012 | Schaller ............. A61B 17/1642 606/79 |
| 2013/0012951 A1 | 1/2013 | Linderman |
| 2013/0018376 A1 * | 1/2013 | Yoon ................. A61B 17/1617 606/79 |
| 2013/0018377 A1 * | 1/2013 | Williams ........... A61B 17/1659 606/85 |
| 2013/0030456 A1 * | 1/2013 | Assell ................ A61B 17/1617 606/170 |
| 2013/0041377 A1 * | 2/2013 | Kuntz ................ A61B 17/1642 606/80 |
| 2013/0150856 A1 * | 6/2013 | Mimran ............. A61B 17/1671 606/79 |
| 2013/0197590 A1 * | 8/2013 | Assell ............. A61B 17/32001 606/300 |
| 2013/0226181 A1 * | 8/2013 | Assell ................ A61B 17/1617 606/79 |
| 2013/0274784 A1 * | 10/2013 | Lenker ............... A61B 17/3417 606/185 |

(56) References Cited

U.S. PATENT DOCUMENTS

| | | | |
|---|---|---|---|
| 2014/0012261 A1* | 1/2014 | Nita | A61B 17/1631 606/79 |
| 2014/0088596 A1* | 3/2014 | Assell | A61B 17/1617 606/79 |
| 2014/0114315 A1* | 4/2014 | Leguidleguid | A61B 17/1659 606/79 |
| 2014/0276832 A1* | 9/2014 | Hibri | A61B 17/1671 606/79 |
| 2015/0134071 A1 | 5/2015 | Luna | |
| 2015/0190149 A1* | 7/2015 | Assell | A61B 17/1671 606/80 |
| 2015/0257770 A1* | 9/2015 | Assell | A61B 17/1617 606/79 |
| 2015/0327872 A1* | 11/2015 | Assell | A61B 17/84 606/279 |
| 2016/0128838 A1* | 5/2016 | Assell | A61B 17/1617 623/17.11 |

FOREIGN PATENT DOCUMENTS

| | | |
|---|---|---|
| FR | 2886839 | 12/2006 |
| JP | 09288239 | 11/1997 |
| JP | 2003522575 | 7/2003 |
| JP | 2003522585 | 7/2003 |
| JP | 2005505315 | 2/2005 |
| JP | 2005152650 | 6/2005 |
| JP | 2006167453 | 6/2006 |
| JP | 2007111538 | 5/2007 |
| JP | 2009542422 | 12/2009 |
| JP | 2010508070 | 3/2010 |
| WO | 0160262 | 8/2001 |
| WO | 2002034147 | 5/2002 |
| WO | 02091909 | 11/2002 |
| WO | 2005039651 | 5/2005 |
| WO | 2007016684 | 2/2007 |
| WO | 2007047065 | 4/2007 |
| WO | 2007142830 | 12/2007 |
| WO | 2008021656 | 2/2008 |
| WO | 2008054752 | 5/2008 |
| WO | 2008060277 | 5/2008 |
| WO | 2008103839 | 8/2008 |
| WO | 2009029074 | 3/2009 |
| WO | 2009108318 | 9/2009 |
| WO | 2009143496 | 11/2009 |
| WO | 2010017631 | 2/2010 |
| WO | 2010065015 | 6/2010 |
| WO | 2012015976 | 2/2012 |

OTHER PUBLICATIONS

Article 94(3) EPC from European Patent Application No. 12722996.1 dated Feb. 3, 2015; 5 pages.
Article 94(3) EPC from European Patent Application No. 13713032.4 dated Jun. 21, 2016; 4 pages.
Article 94(3) EPC from European Patent Application No. 13713032.4 dated Nov. 16, 2015; 5 pages.
Chinese Office Action with English translation from Chinese Patent Application No. 2010800606331 dated Jul. 31, 2014; 24 pages.
English translation of Japanese Notification of Reasons for Refusal from Japanese Patent Application No. 2012-548030 dated Mar. 13, 2015; 2 pages.
English translation of Japanese Notification of Reasons for Refusal from Japanese Patent Application No. 2014-509508 dated Mar. 11, 2016; 4 pages.
Japanese Notification of Reasons for Refusal with English translation from Japanese Patent Application No. 2012-548030 dated Sep. 9, 2014; 3 pages.
Korean Notice of Final Rejection with English translation from Korean Patent Application No. 10-2012-7019264 dated Mar. 14, 2016; 6 pages.
PCT Search Report and Written Opinion from International Application No. PCT/US2013/031669 dated May 7, 2013; 10 pages.
PCT Search Report and Written Opinion from International Patent Application No. PCT/US2010/061807 dated May 20, 2011; 23 pages.
PCT Search Report and Written Opinion from International Patent Application No. PCT/US2012/036774 dated Aug. 10, 2012; 9 pages.

* cited by examiner

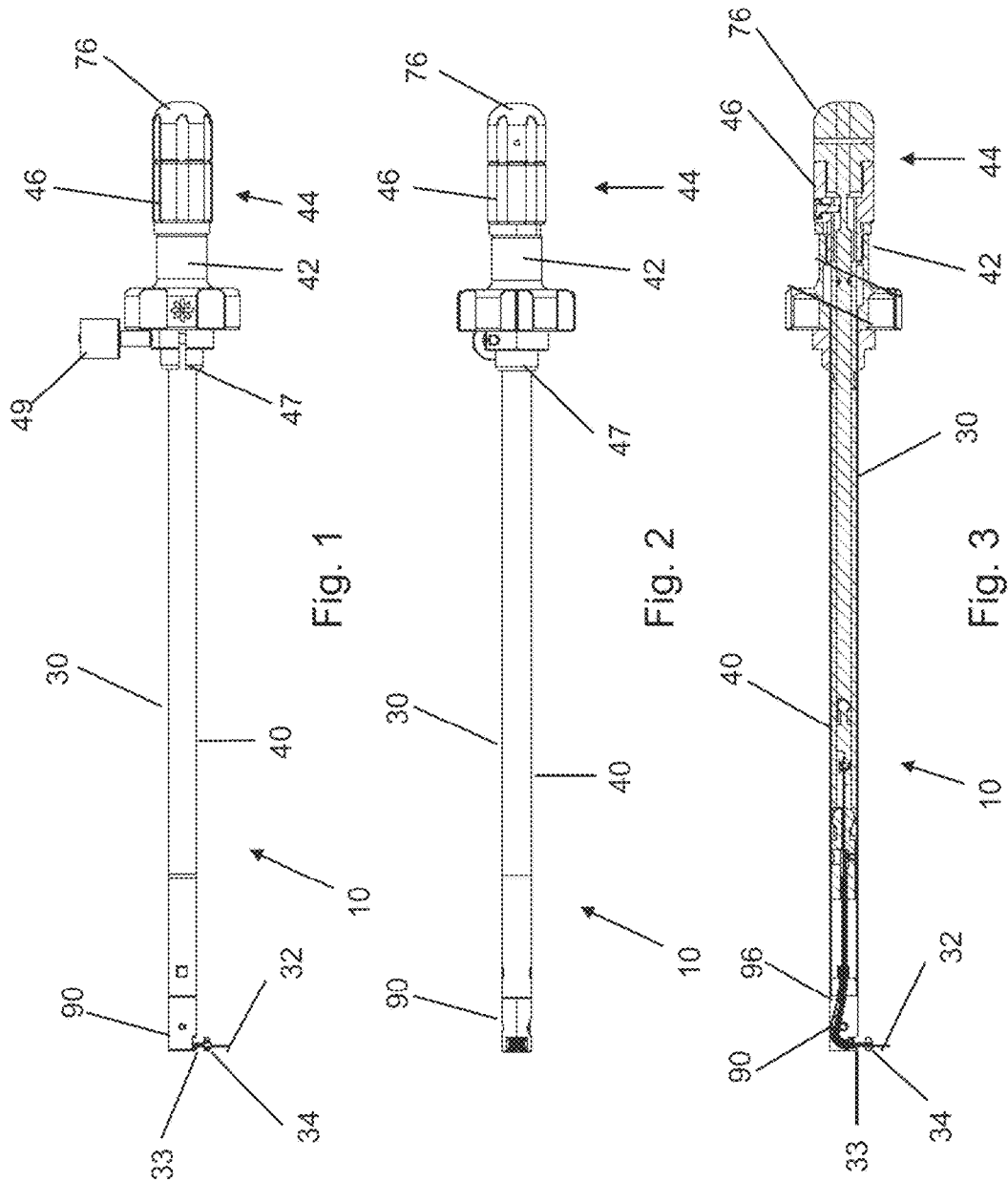

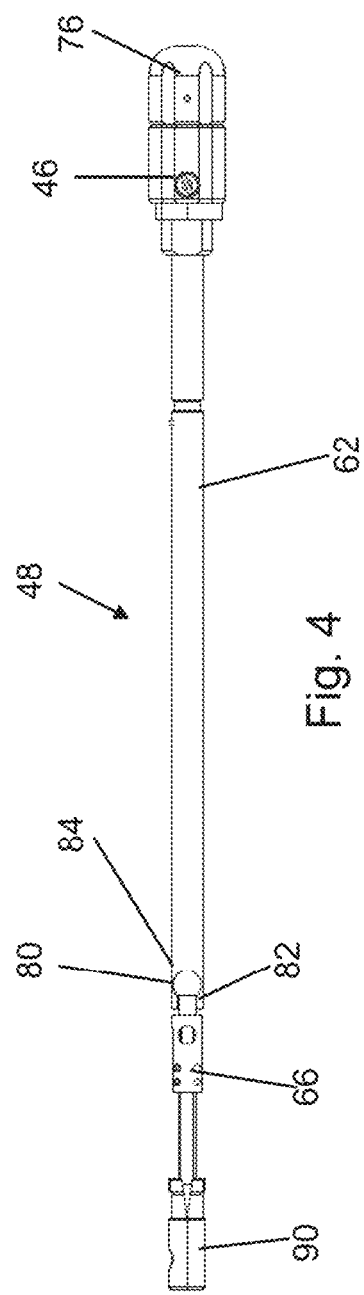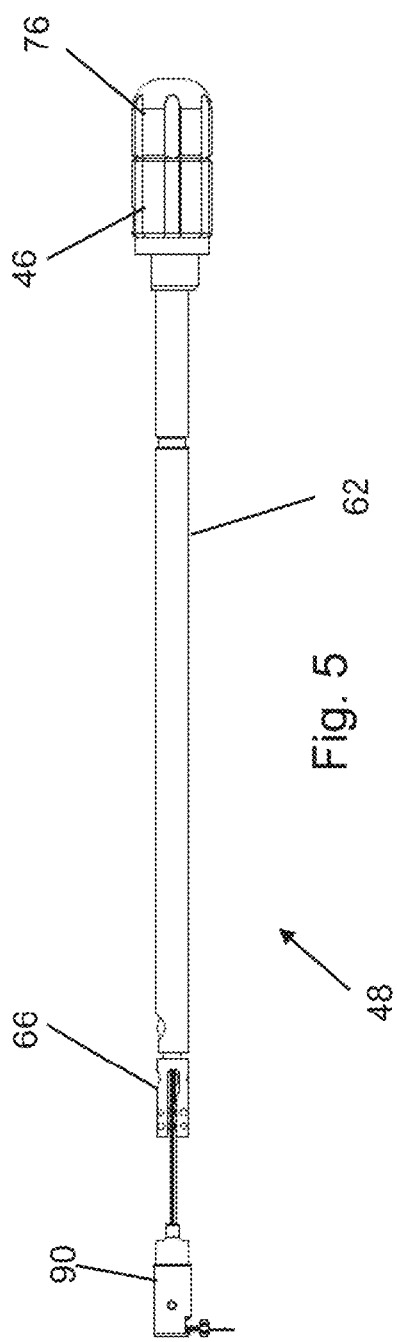

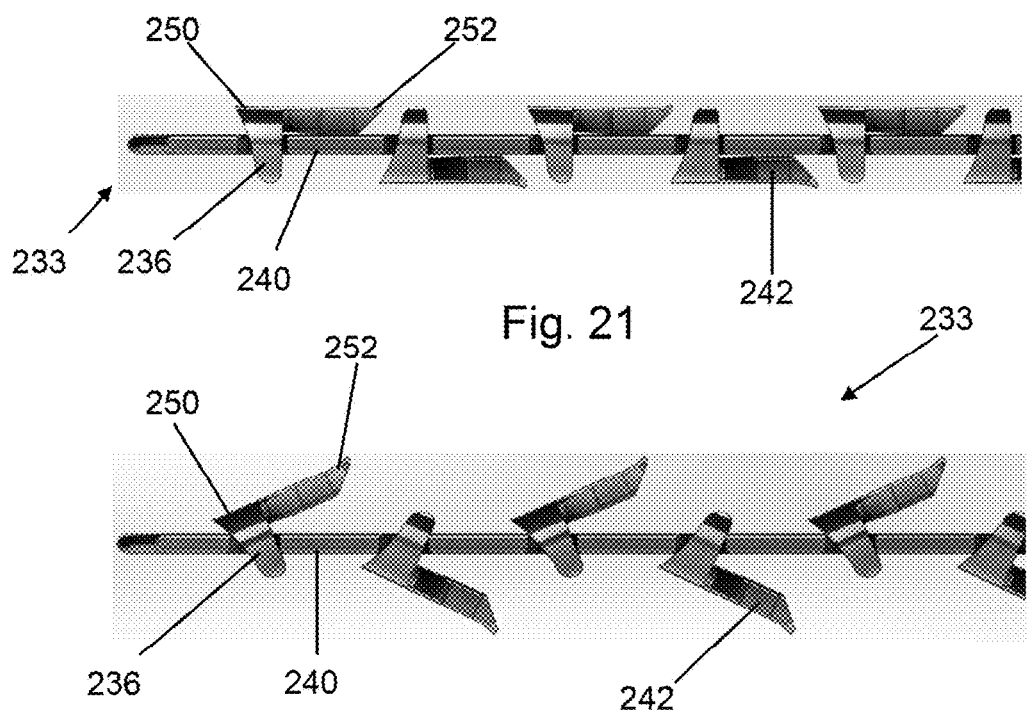
Fig. 21
Fig. 22
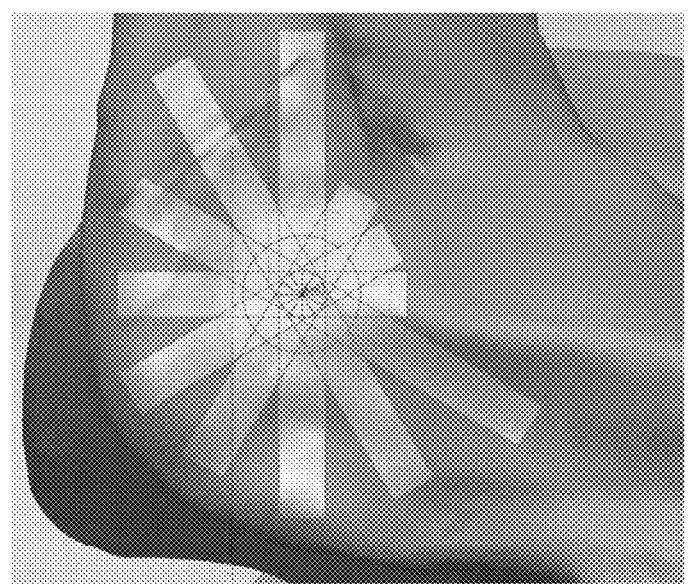
Fig. 23

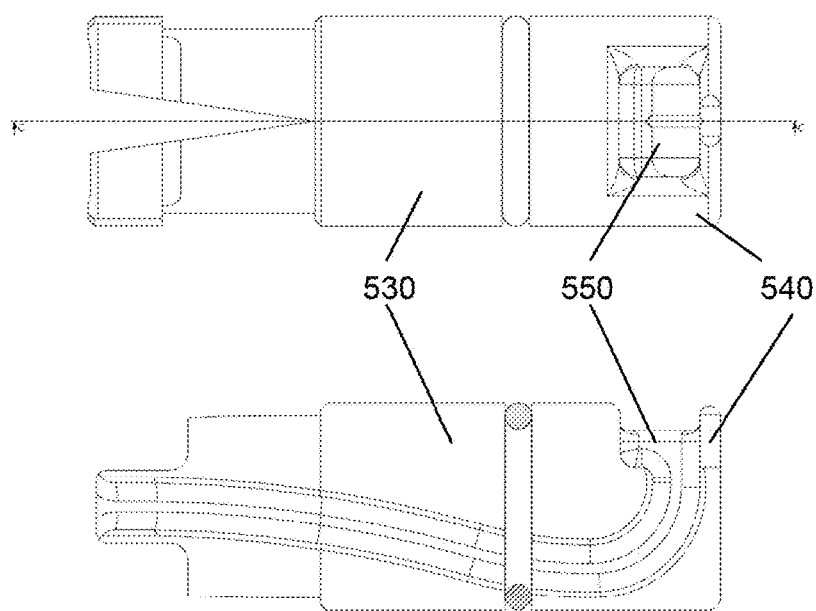
Fig. 26
Fig. 27
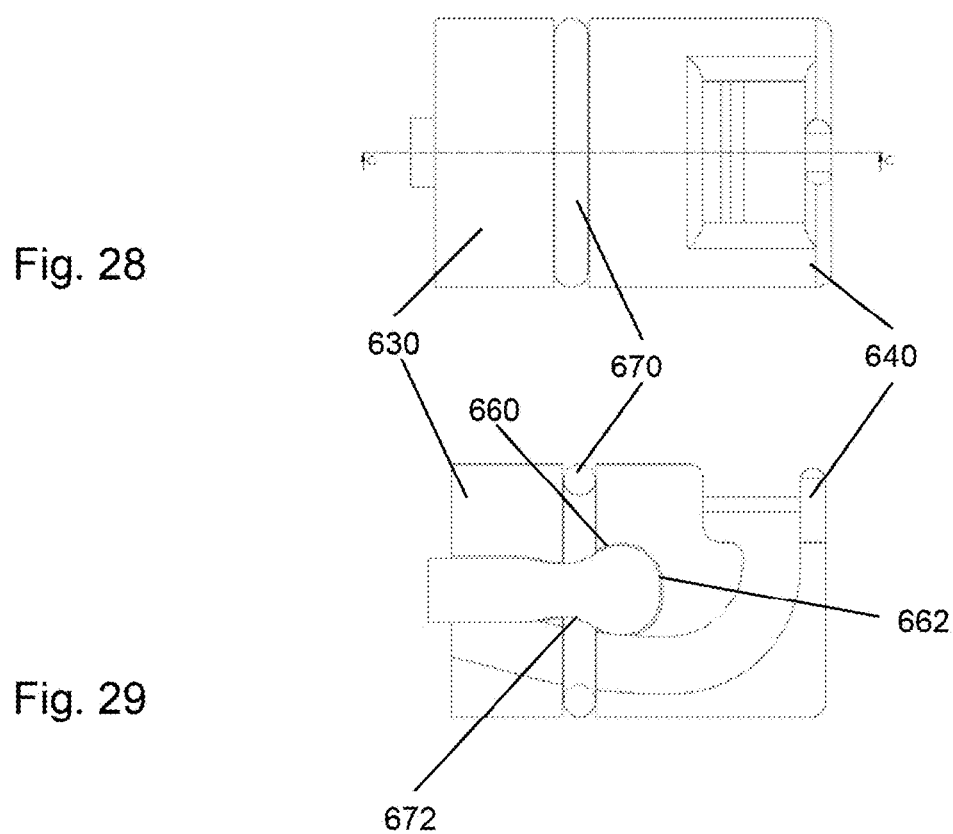
Fig. 28
Fig. 29

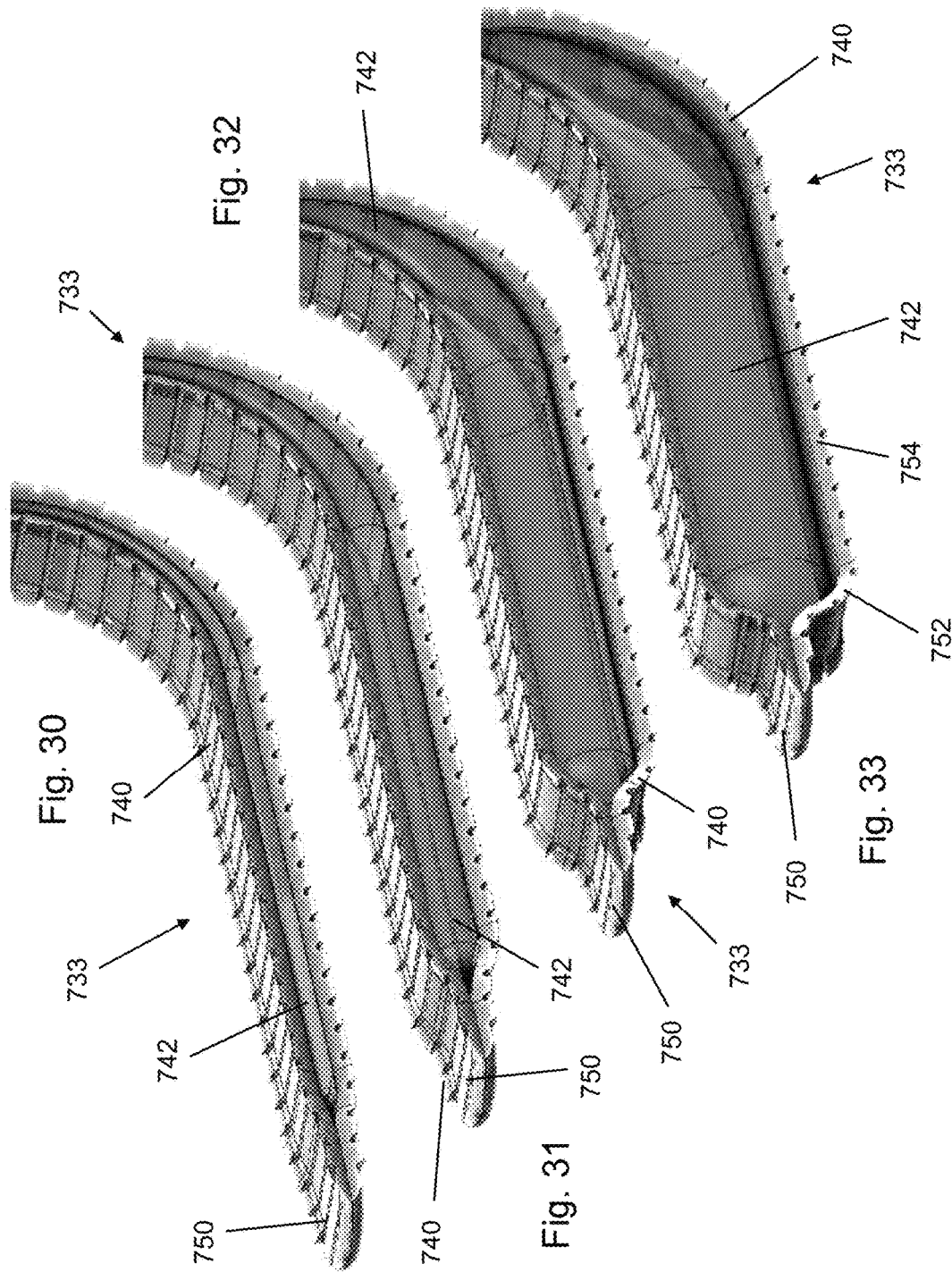

UNDERCUTTING SYSTEM FOR USE IN CONJUNCTION WITH SACROILIAC FUSION

REFERENCE TO RELATED APPLICATION

This application is a divisional of U.S. Pat. No. 9,861,375, issued Jan. 9, 2018, and claims priority to U.S. Provisional Application No. 61/925,280, which was filed on Jan. 9, 2014, the contents of which are incorporated herein by reference.

FIELD OF THE INVENTION

An embodiment of the invention is directed to a method for treating patients experiencing sacroiliac joint pain. More particularly, the invention relates to a system for preparing a space between the sacrum and the iliac to facilitate sacroiliac joint fusion.

BACKGROUND OF THE INVENTION

The sacroiliac joint is located at the intersection of the ilium, the upper bone of the pelvis, and the sacrum at the base of the spine. One of the primary functions of the sacroiliac joint is to provide shock absorption of pressures put on the spine.

Certain persons experience pain in the sacroiliac joint. This pain may result from a variety of causes, examples of which include injuries, incorrect vertebra fusion during pre-birth development and effects of pregnancy.

If initial efforts to reduce the pain in the sacroiliac joint through physical therapy and/or steroid injections are not effective, surgery may be needed to fuse together the sacroiliac joint. One typical surgical technique involves forming an incision in the lower back over the sacroiliac joint. The articular cartilage is removed from both surfaces. This process is also called chondrectomy.

The sacrum and the ilium are held together with screws or a plate. Eventually, bone grows between the sacrum and the ilium to thereby fuse together the sacroiliac joint. Because of the challenges in accessing the surfaces of the sacrum and the ilium that will fuse together, this type of surgery may result in damage to tissue, nerves and/or blood vessels that surround the sacroiliac joint. Such damage may prevent the patient from fully realizing the benefits of the sacroiliac joint fusion and in some instances cause the patient to experience more pain after the sacroiliac joint fusion than before the sacroiliac joint fusion.

SUMMARY OF THE INVENTION

An embodiment of the invention is directed to an undercutting system for preparing a region between an ilium and a sacrum for sacroiliac fusion. The undercutting system includes an insertion apparatus and a cutting assembly.

The cutting assembly is operably mounted with respect to the insertion apparatus. The cutting assembly has a distal end and a proximal end. The cutting assembly includes a plurality of cutting elements and a cutting element attachment mechanism.

The cutting element attachment mechanism engages the cutting elements to operably mount the cutting elements with respect to the insertion apparatus. The cutting element attachment mechanism permits the cutting elements to pivot with respect to each other.

Another embodiment of the invention is directed to an undercutting system for preparing a region between an ilium and a sacrum for sacroiliac fusion. The undercutting system includes an insertion apparatus and a cutting assembly. The cutting assembly is operably mounted with respect to the insertion apparatus.

The cutting assembly has a distal end and a proximal end. The cutting assembly includes an elongated base and a plurality of cutting element. The elongated base is fabricated from a flexible material. The plurality of cutting elements is movable with respect to the elongated base. The cutting elements are configured to cut on at least one of moving towards the distal end or the proximal end of the cutting assembly.

Another embodiment of the invention is directed to an undercutting system for preparing a region between an ilium and a sacrum for sacroiliac fusion. The undercutting system includes an insertion apparatus and a cutting assembly. The cutting assembly is movable with respect to the insertion apparatus between a retracted configuration and an extended configuration. In the extended configuration at least a portion of the cutting assembly extends from the insertion apparatus. The cutting assembly has a plurality of kerfs formed therein. The kerfs are oriented at an angle with respect to an upper surface of the cutting assembly.

Another embodiment of the invention is directed to a method of preparing a region between adjacent bones for fusion. A first aperture is formed in one of the bones. Wherein the at least one aperture extends through one of the bones. An undercutting system is inserted into the first aperture. The undercutting system includes an insertion apparatus and a cutting assembly. A first path is cut between the adjacent bones by extending or retracting the cutting assembly with respect to the insertion apparatus.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 1 is a side view of an undercutting system for use in a sacroiliac fusion procedure.

FIG. 2 is a bottom view of the undercutting system of FIG. 1.

FIG. 3 is a sectional view of the undercutting system taken along a line 3-3 in FIG. 2.

FIG. 4 is a side view of a control mechanism for use in the undercutting system of FIG. 1.

FIG. 5 is a top view of the control mechanism of FIG. 4.

FIG. 21 is a side view of the cutting assembly from the undercutting system of FIG. 19 where the cutting assembly is in the insertion configuration.

FIG. 22 is a side view of the cutting assembly from the undercutting system of FIG. 19 where the cutting assembly is in the retraction configuration.

FIG. 23 is a top view of the undercutting system of FIG. 19 used to form a plurality of paths between an ilium and a sacrum in a patient.

FIG. 26 is a front view of an alternative embodiment of a distal end of the insertion apparatus.

FIG. 27 is a sectional view of the insertion apparatus taken along a line C-C in FIG. 26.

FIG. 28 is a front view of an alternative embodiment of a distal end of the insertion apparatus.

FIG. 29 is a sectional view of the insertion apparatus taken along a line C-C in FIG. 28.

FIG. 30 is a perspective view of an alternative embodiment of the cutting assembly in a retracted configuration.

FIG. 31 is a perspective view of the cutting assembly of FIG. 30 in a first partially expanded configuration.

FIG. 32 is a perspective view of the cutting assembly of FIG. 30 in a second partially expanded configuration.

FIG. 33 is a perspective view of the cutting assembly of FIG. 30 in a fully expanded configuration.

DETAILED DESCRIPTION OF THE PREFERRED EMBODIMENTS

Figure 10:
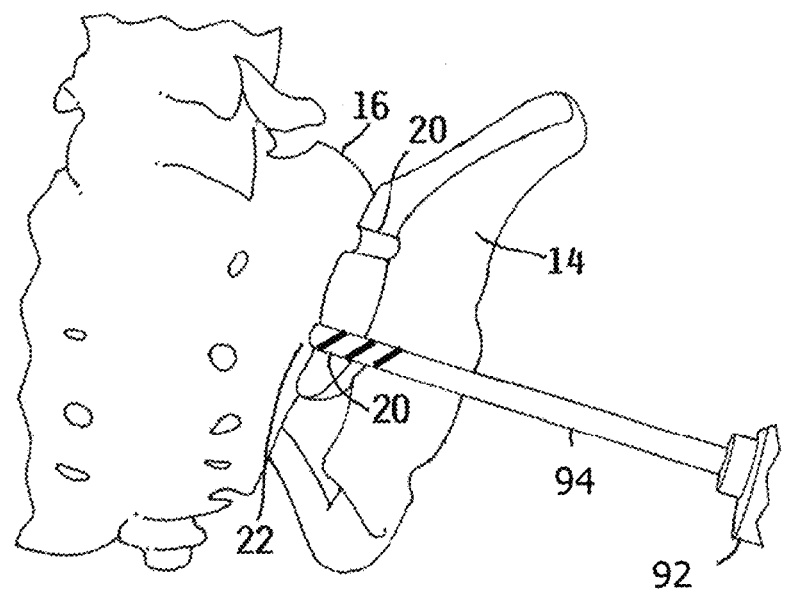
FIG. 10 is a partially cut away perspective view of an aperture being drilled in the sacrum and the ilium as an initial step in a sacroiliac fusion procedure.

An embodiment of the invention is directed to an undercutting system 10, such as is illustrated in FIGS. 1-3. The undercutting system 10 may be used for preparing surfaces of the ilium 14 and the sacrum 16 for sacroiliac joint fusion, which are illustrated in FIG. 10. The undercutting system utilizes an aperture 20 formed in the ilium 14 to access a region 22 between the ilium 14 and the sacrum 16.

A person of skill in the art will appreciate that the undercutting system 10 may be used in other surgical applications where it is desired to remove tissue between two bones that are located in close proximity to each other especially where it is not possible or desirable to directly access the tissue between the two bones utilizing a lateral approach.

In certain embodiments, the aperture 20 may have a diameter of up to about 50 millimeters. In other embodiments, the aperture 20 may have a diameter of between about 6 millimeters and 15 millimeters.

The undercutting system 10 thereby enables tissue such as cartilage to be removed from the adjacent surfaces of the ilium 14 and the sacrum 16 and for at least a portion of the adjacent surfaces of the ilium 14 and the sacrum 16 to be removed or otherwise disturbed. This procedure may be referred to as preparing bleeding bone surfaces on the ilium 14 and the sacrum 16, which are more receptive to growing bone between them as part of sacroiliac joint fusion.

Thereafter, the ilium 14 and the sacrum 16 may be held in a stationary position with respect to each other such as with a screw that is extended through the aperture 20, as is discussed in more detail below. Maintaining the ilium 14 and the sacrum 16 in the stationary position facilitates bone growth between the ilium 14 and the sacrum 16 to thereby fuse the sacroiliac joint.

Performing the sacroiliac fusion using the undercutting system 10 disclosed herein reduces the complexity of the sacroiliac fusion when compared to prior techniques used for sacroiliac fusion and thereby has the potential to decrease the patient recovery time from the sacroiliac fusion procedure.

Additionally, sacroiliac fusion performed using the concepts described herein has the potential of fewer side effects because this process does not require the surgeon to work proximate the nerves and/or blood vessels, as is done with prior sacroiliac fusion techniques.

Furthermore, the apparatus and technique disclosed herein do not formally expose the sacroiliac joint during the process of preparing the sacroiliac joint for fusion and thereby reduces the potential of infection. The time associated with preparing the surfaces of the ilium and the sacrum is also reduced when compared to the prior more invasive techniques used to prepare the sacroiliac joint for fusion.

The undercutting system 10 may include an insertion apparatus 30 and a probe assembly 32 that extends from a distal end of the insertion apparatus 30, as illustrated in FIGS. 1-3. The insertion apparatus 30 may include an elongated shaft 40 that is formed with a length that enables a proximal end thereof to be positioned outside of the patient's body while a distal end thereof is utilized to the prepare the region between the ilium 14 and the sacrum 16 for the sacroiliac fusion process. In certain embodiments, the length of the elongated shaft 40 is between about 15 centimeters and about 45 centimeters.

The probe assembly 32 may have a relatively flat configuration and be formed from a flexible and strong material that resists breakage. An example of one such material is nitinol. A beneficial quality of nitinol is that nitinol is bendable but returns to the unbent configuration when the force that caused the bending is removed, even at high strains. The probe assembly 32 is intended to pass through the tissue between the ilium 14 and the sacrum 16 and thereby define a path through the tissue for the subsequent cutting operation.

As such, the probe assembly 32 should be sufficiently sharp to cut through the tissue between the ilium 14 and the sacrum 16 while not being sharp enough such that the probe assembly 32 has a tendency to cut into the ilium 14 or the sacrum 16. The edges of the probe assembly 32 may be sharp enough to cut through this tissue without any additional sharpening.

A distal end of the probe assembly 32 may be curved but not sharpened to facilitate the probe assembly 32 being extended from the insertion apparatus 30 to define a path through the tissue but without cutting into the ilium 14 and the sacrum 16 during the extension process.

The probe assembly 32 may include more than one layer. Utilizing multiple layers enables the probe assembly 32 to exhibit enhanced flexibility when compared to a single layer configuration. In a multi-layer configuration, one of the layers may be thicker. This layer would be viewed as the primary and the other layer(s) would be viewed as the auxiliary layer(s).

In certain embodiments, the main layer may have a thickness that is between about 30% and about 60% greater than the thickness of the auxiliary layer(s). In other embodiments, the main layer may have a thickness that is about 50% thicker than the thickness of the auxiliary layer(s).

The main layer may have a thickness of between about 0.010 inches and about 0.030 inches. In other embodiments, the main layer has a thickness of about 0.018 inches. The auxiliary layer may have a thickness of between about 0.010 inches and about 0.030 inches. In other embodiments, the auxiliary layer has a thickness of about 0.013 inches.

While it is not illustrated that the main layer and the auxiliary layer are attached to a separate control mechanism than the cutting assembly, it is possible for separate controls to be used with the main layer and the auxiliary layer to enable independent extension and retraction of the main layer and the auxiliary layer.

The elongated shaft 40 may be formed with a relatively small outer diameter to minimize a size of the aperture 20 that needs to be formed in the ilium 14. The larger the aperture 20 that is formed in the ilium 14, the greater the fastener size required to gain adequate purchase in the ilium. In certain embodiments, the outer diameter of the elongated shaft 40 is between about 6 millimeters and 15 millimeters.

The insertion apparatus 30 may also include a handle portion 42 proximate a proximal end thereof. The handle portion 42 enhances the ability to manipulate the insertion apparatus 30 such as insertion, rotation and withdrawal.

The handle portion 42 may have a diameter that is greater than a diameter of the elongated shaft 40. In certain embodiments, the handle portion 42 has a diameter of between about 1 centimeter and about 3 centimeters.

An outer edge of the handle portion 42 may have a plurality of concave or convex regions 44 formed therein, or may be made of an elastomeric material. The concave regions 44 or elastomeric material enhance the ability to grip the handle portion 42 and thereby manipulate the insertion apparatus 30.

The insertion apparatus 30 may further include a control knob 46 that is used for extending and retracting the cutting assembly 33. In one configuration of the insertion apparatus 30, the control knob 46 is rotatably mounted with respect to the insertion apparatus 30.

The control knob 46 may have a diameter that is different than a diameter of the handle portion 42. Forming the control knob 46 with a diameter that is different than a diameter of the handle portion 42 minimizes the potential that a person using the insertion apparatus 30 would inadvertently manipulate the insertion apparatus 30 or the control knob 46.

The control knob 46 may have a diameter that is less than a diameter of the handle portion 42. In certain embodiments, the control knob 46 has a diameter of between about 1 centimeter and about 3 centimeters.

An outer edge of the control knob 46 may have a plurality of concave regions formed therein or may contain an elastomeric material. The concave regions or elastomeric material enhance the ability to grip the control knob 46 and thereby manipulate the insertion apparatus 30.

Rotation of the control knob 46 in a first direction causes the cutting assembly 33 to be extended from the distal end of the insertion apparatus 30. Rotation of the control knob 46 in a second direction, which is opposite the first direction, causes the cutting assembly 33 to be retracted into the distal end of the insertion apparatus 30.

As an alternative or in addition to manually using the control knob 46 to cause retraction of the probe assembly 32, it is possible to use an automated mechanism in the undercutting system that causes retraction of the probe assembly 32.

The automated mechanism can reduce the potential of the probe assembly 32 getting hung up if the probe assembly 32 is not at least partially retracted while the cutting assembly 33 is extended from the insertion apparatus 30.

The insertion apparatus 30 may also include a locking collar 47 that is operably attached thereto. The locking collar 47 may be slidably mounted onto the elongated shaft 40 and may initially be positioned proximate the handle portion 42.

The locking collar 47 may be tightened such that the collar 47 locks in position along the elongated shaft 40 at a point between the probe assembly 32 and the control knob 46 by, for example, tightening a thumb screw 49.

The locking collar 47 thereby retains the shaft the elongated shaft 40 in a fixed position with respect to a docked working cannula 51 to prevent movement of the insertion apparatus 30 further into the ilium in the case of drilling past the sacral cortex.

Loosening the locking collar 47 by, for example, loosening the screw 49, allows the locking collar 47 to slide along the elongated shaft 40 thereby allowing adjustment of the depth of shaft 40 as required.

Inside at least a portion of the elongated shaft 40 is a control mechanism 48 that operably attaches the cutting assembly 33 to the other portions of the insertion apparatus 30, as most clearly illustrated in FIGS. 4 and 5. A primary function of the control mechanism 48 is to facilitate extension and retraction of the cutting assembly 33.

The control mechanism 48 may generally include an attachment section 62 that attaches directly to the cutting assembly 33. The attachment section 62 is attached to the control knob 46. In one configuration, the attachment section 62 is fixedly attached to the control knob 46 so that the first section 62 rotates when the control knob 46 is rotated.

The attachment section 62 may have a length that is less than the length of the elongated shaft 40. In certain embodiments, the attachment section 62 has a length that is approximately one-half of the length of the elongated shaft 40.

The attachment section 62 may have a generally cylindrical shape with an outer diameter that is slightly smaller than an inner diameter of the elongated shaft 40. Forming the attachment section 62 with this shape facilitates rotating and sliding of the attachment section 62 with respect to the elongated shaft 40.

A distal end of the attachment section 62 has a connection mechanism 66 that facilitates attaching the cutting assembly 33 to the attachment section 62. In one such configuration, the connection mechanism 66 includes a recess 70 formed in the distal end. The recess 70 may have a width and a depth that is greater than a width and a depth of the proximal end of the cutting assembly 33.

An attachment pin 72 may be provided in the recess 70 that enables the cutting assembly 33 to engage the connection mechanism 66. In certain embodiments, the attachment pin 72 may be oriented generally perpendicular to the attachment section 62.

An aperture may be formed in the proximal end of the cutting assembly 33. The aperture may have a diameter that is slightly larger than a diameter of the attachment pin. Using such a configuration, the attachment pin may extend into the aperture to retain the attachment section 62 in a fixed relationship with respect to the cutting assembly 33.

Forming the connection mechanism 66 with preceding configuration allows the cutting assembly 33 to be attached to the attachment section 62 when the attachment section 62 and the cutting assembly 33 are not covered by the elongated shaft 40.

On the other hand, when the elongated shaft 40 is placed over attachment section 62 and the cutting assembly 33, the cutting assembly 33 is retained in engagement with the attachment section 62.

A person of skill in the art will appreciate that it is possible to attach the attachment section 62 and the cutting assembly 33 using different structures, which enable sliding and rotating of the attachment section 62 with respect to the elongated shaft 40.

While the figures illustrate that a mechanical connection is provided between the probe assembly 32 and the other components of the undercutting system 10, it is also possible to utilize an electrical connection between the probe assembly 32 and the other components of the undercutting system 10. Such an electrical connection may utilize switches and actuators. It is also possible to use pneumatic and hydraulic systems to operably connect the probe assembly 32 and the other components of the undercutting system 10.

The connection mechanism 66 may also include a ball-type connector 80 that attaches the connection mechanism 66 to the attachment section 62. The ball-type connector 80 may include a ball-shaped extension 82 on the connection mechanism 66 and a recess 84 formed in the distal end of the attachment section 62. The recess 84 has a shape that is generally complementary to the shape of the ball-shaped extension 82.

Similar to the attachment between the connection mechanism 66 and the cutting assembly 33, the ball-type connector 80 allows the attachment section 62 to be attached to the connection mechanism 66 when the attachment section 62 and the connection mechanism 66 are not covered by the elongated shaft 40.

On the other hand, when the elongated shaft 40 is placed over attachment section 62 and the connection mechanism 66, the ball-shaped extension 82 is retained in engagement with the recess 84.

Alternatively or additionally, the undercutting system 10 may include more than one attachment section 62 having different lengths. Using such a configuration enables one of the attachment sections 62 to be selected based upon the length of the probe assembly 32.

A benefit of using the ball-shaped extension 82 is that this connection mechanism enables the control handle to rotate such as when extending or retracting the probe assembly 32 with respect to the insertion apparatus 30 without having the probe assembly 32 rotate.

The cutting assembly 33 may be formed with a height and a width that are both slightly smaller than a height and a width of a channel 96 that is formed in an end cap 90, which is discussed in more detail below. Forming the cutting assembly 33 with these dimensions enables the cutting assembly 33 to slide in the channel 96.

The cap 90 may be positioned in the distal end of the elongated shaft 40, as most clearly illustrated in FIG. 3. The cap 90 thereby seals the elongated shaft 40 to generally restrict tissue and fluid from entering the elongated shaft 40.

While it is possible for a distal end of the cap 90 to be oriented generally transverse to the elongated shaft 40, the distal end of the cap 90 may be oriented at an angle of less than about 90 degrees with respect to the elongated shaft 40. In certain embodiments, the distal end of the cap 90 is oriented at an angle of between about 45 degrees and about 60 degrees.

As referenced above, the cap 90 has the channel 96 formed therein. Proximate the proximal end, the channel 96 may be generally aligned with but offset from a central axis of the elongated shaft 40. Proximate the distal end, the channel 96 may be oriented generally perpendicular to the central axis of the elongated shaft 40 and having a pocket 98 to house the main cutter portion 60 and a cutter extension portion 61. The pocket 98 may have a length and/or a width that are larger than the length and/or width of the channel 96.

Intermediate the proximal end and the distal end, the channel 96 is curved. The radius of curvature may be determined by a variety of factors. An example of one such factor is the flexibility of the portion of the probe assembly 32 and the flexibility of a cutting assembly 33, which is described in more detail below.

The channel 96 thereby causes the probe assembly 32 to be deflected such that when the probe assembly 32 extends from the cap 90, the probe assembly 32 is oriented in a direction that is generally transverse to the elongated shaft 40, as illustrated in FIG. 3. This configuration enables the probe assembly 32 to extend into the region between the ilium 14 and the sacrum 16.

Because of the flexibility of the cutting assembly 33 and probe assembly 32, it is not necessary that the distal end of the channel 96 be oriented precisely transverse to the central axis of the elongated shaft 40. For example, the distal end of the channel 96 may be oriented slightly towards the ilium 14 to encourage preferential cutting of the ilium 14 because the ilium 14 is harder than the sacrum 16. Alternatively, orienting the distal end of the channel 96 slightly towards the sacrum 16 may encourage preferential cutting of the sacrum 16 and allow the angle of curvature within the cap to be reduced.

As an alternative to, or in conjunction with, utilizing flexibility of the probe assembly 32 and/or the cutting assembly 33 to facilitate tracking of the joint between the ilium 14 and the sacrum 16, it is possible for at least a portion of the cap 90 to swivel. The cap could track the joint itself, or could track a ring on a guide at the bottom of the insertion apparatus 30.

Such a configuration enables the user to angle the guide to align the guide with the joint as viewed using an imaging technique such as fluoroscopy. Once a proper alignment is obtained, the guide may be locked into place so that the probe assembly 32 and the cutting assembly tracks the guide.

In certain embodiments, the cap 90 is fabricated from a radio lucent material such as aluminum. Fabricating the cap 90 in this manner enables imaging such as fluoroscopy to be used to monitor the location of the end of the cutting assembly 33 throughout the undercutting process such as when the distal end of the cutting assembly 33 is in the retracted position.

The cap 90 may have a positive feature that is generally perpendicular to the axis of the elongated shaft 40. The elongated shaft 40 may also include an aperture that is generally aligned with the positive feature when the cap 90 is placed into the distal end of the elongated shaft 40. A screw is extended across the cap 90 thereby forcing the positive feature of the cap 90 into the aperture in the elongated shaft 40 retaining the cap 90 in a stationary position with respect to the elongated shaft 40.

The cutting assembly 33 may be used in conjunction with the probe assembly 32. As is described in more detail herein, the probe assembly 32 facilitates identifying the joint line between the ilium 14 and the sacrum 16. Thereafter, the cutting assembly 33 cuts tissue between the ilium 14 and the sacrum 16 to prepare for the sacroiliac fusion.

To permit the deflection of the cutting assembly 33, the cutting assembly 33 may be fabricated from a flexible material, as is discussed in more detail below. To increase the flexibility of the cutting assembly 33, a plurality of kerfs or notches 53 may be formed in the cutting assembly 33.

While the kerfs 53 are utilized to provide flexibility to the cutting assembly 33, the number and placement of the kerfs 53 should be selected to minimize negative impact on the strength of the cutting assembly 33.

Figure 6:
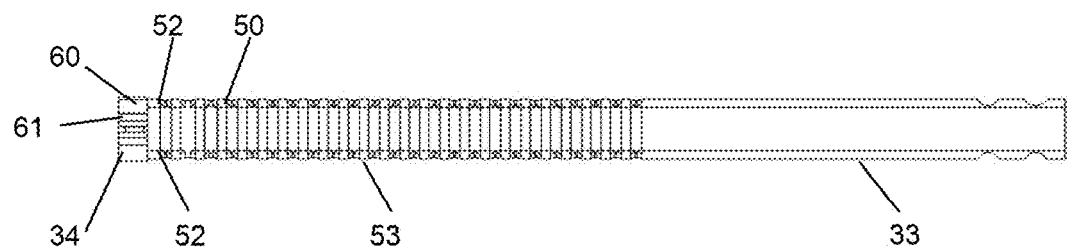
FIG. 6 is a top view of a cutting assembly for use in the undercutting system of FIG. 1.
Figure 7:
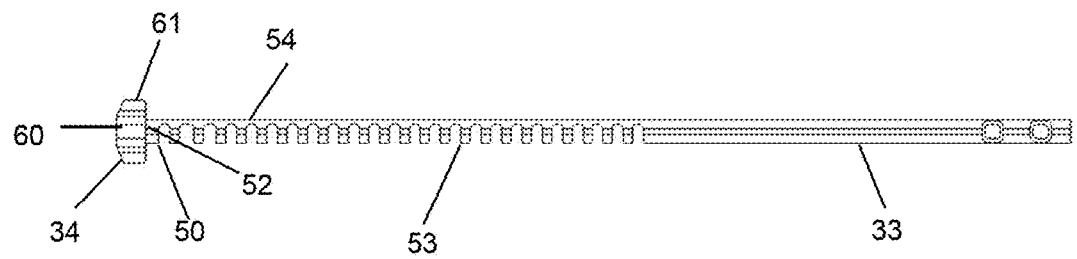
FIG. 7 is a side view of the cutting assembly of FIG. 6.

As illustrated in FIGS. 6 and 7, the kerfs 53 may extend through an upper surface 50 of the cutting assembly 33. The kerfs 53 may also extend through at least a portion of at least one of the side surfaces 52 of the cutting assembly 33. In certain embodiments, the kerfs 53 extend substantially through both of the side surfaces 52. The kerfs 53 may also extend into a lower surface 54 of the cutting assembly 33.

Forming the kerfs 53 with the preceding configuration allows a lower surface 54 of the cutting assembly 33 to be substantially continuous. This configuration provides the cutting assembly 33 with sufficient strength to resist breaking while the cutting assembly 33 is used to cut tissue from between the ilium 14 and the sacrum 16.

The kerfs 53 may be formed with a width that is sufficiently large so that the material remaining between the kerfs 53 does not impinge upon itself while the cutting assembly 33 is deflected from the initial orientation that is generally aligned with but offset from the center axis of the insertion apparatus 30 to a deflected orientation that is generally transverse to the central axis of the insertion apparatus, as the cutting assembly 33 exits the distal end of the cap 90.

In certain embodiments, the kerfs 53 may have a width of up to about 1.5 millimeters. In other embodiments, the kerfs 12 may have a width that is between about 0.6 millimeters and about 1 millimeter.

The kerfs 53 also decrease the smoothness of the cutting assembly 33. Contact between the kerfs 53 and the tissue between the ilium 14 and the sacrum 16 could cause such tissue to be abraded or cut and thereby facilitate preparation of the region between the ilium 14 and the sacrum 16 for the sacroiliac fusion process.

While the figures illustrate that the kerfs 53 are formed on one side of the cutting assembly 33, it is possible for the kerfs 53 to be formed on both sides of the cutting assembly 33. If the kerfs 53 are formed on both sides of the cutting assembly 33, the kerfs 53 on the opposite sides may be offset so that the kerfs 53 do not unduly weaken the cutting assembly 33.

Whether the kerfs 53 are formed in one side or both sides of the cutting assembly 33, the kerfs 53 should not occupy too great a portion of the cutting assembly 33 such that the cutting assembly 33 is likely to bend or kink during the process of deflecting during the extension or retraction of the cutting assembly 33 from the insertion apparatus 30 as well as during the use of the cutting assembly 33 to cut tissue from between the ilium 14 and the sacrum 16.

Figure 8:
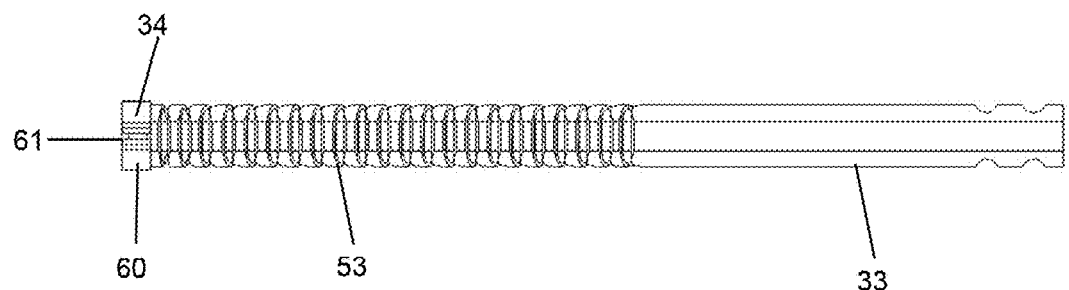
FIG. 8 is a top view of an alternative configuration of the cutting assembly.
Figure 9:
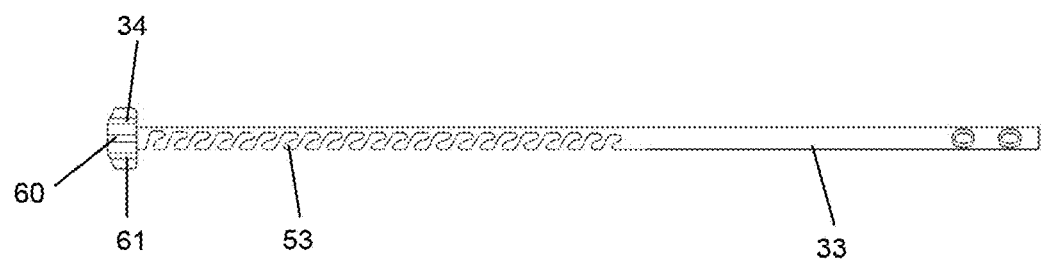
FIG. 9 is a side view of the cutting assembly of FIG. 8.

An alternative embodiment of the invention utilizes kerfs 53 having an angular configuration, as illustrated in FIGS. 8 and 9, which is to be distinguished from the kerfs 53 that are oriented generally perpendicular to a lower surface of the cutting assembly 33, as illustrated in FIGS. 6 and 7.

The angle of the kerfs 53 may be between about 20 degrees and about 70 degrees. In certain embodiments, the angle of the kerfs 53 is between about 25 degrees and about 35 degrees. In still other embodiments, the angle of the kerfs 53 is about 30 degrees.

Each kerf 53 may have a thickness that is substantially constant between a proximal end and a distal end thereof. In other embodiments, the kerfs 53 have a thickness that is greater proximate the distal end than proximate the proximal end, as illustrated in FIG. 8. In certain embodiments, the thickness of each kerf 53 proximate the distal end is about twice the thickness of the kerf 53 proximate the proximal end.

Similar to the embodiment illustrated in FIGS. 6 and 7, the spacing between adjacent kerfs 53 should be sufficiently large such that material between adjacent kerfs 53 does not impinge upon itself when the cutting assembly 33 is moved from the retracted position where the cutting assembly 33 is oriented generally parallel to the central axis of the insertion apparatus 30 to the extended position where at least the distal portion of the cutting assembly 33 is oriented generally perpendicular to the central axis of the insertion apparatus 30.

In certain embodiments, the thickness of the kerf 53 proximate the distal end may be greater than a separation between adjacent kerfs 53 and the thickness of the kerf 53 proximate the distal end may be less than a separation between adjacent kerfs 53.

The separation between adjacent kerfs 53 may be between about 0.5 millimeters and about 0.75 millimeters. In other embodiments, the separation between adjacent kerfs 53 is about 0.6 millimeters.

The thickness of the kerf 53 proximate the distal end may be between 0.5 millimeters and about 0.9 millimeters. In other embodiments, the thickness of the kerf 53 proximate the distal end is about 0.7 millimeters. Between about 20% and about 80% of the length of the kerf 53 has the greater thickness. In other embodiments, between about 30% and 50% of the length of the kerf 53 has the greater thickness.

The corners between the wide and narrow sections of the kerf 53 and proximate the intersection of the kerf 53 and the lower surface 54 may be rounded. In certain embodiments, the rounded corners have a radius of between about 0.125 millimeters and about 0.5 millimeters. In other embodiments, the radius is about 0.25 millimeters.

The embodiment of the cutting assembly 33 illustrated in FIGS. 6 and 7 could be modified to include the kerfs 53 having a thickness that is greater proximate the distal end than the proximal end thereof as illustrated by the left most opening on the cutting assembly illustrated in FIG. 7.

Forming the kerf 53 with the preceding configuration enhances the amount of the lower surface 54 of the cutting assembly 33 to which the side surfaces 52 have been removed, which thereby increases the length of the lower surface 54 that is bent. This configuration decreases stress concentrations and the associate metal fatigue and thereby increases the useful life of the cutting assembly 33.

The cutting assembly 33 may be supported by the probe assembly 32, which extends through the cutting assembly 33, to thereby enhance the strength of the cutting assembly 33. The cutting assembly 33 having the preceding shape and characteristics may be formed from a variety of materials. A person of skill in the art will appreciate that the material used to fabricate the cutting assembly 33 should be suitable for use within a human body. An example of one such material for fabricating the cutting assembly 33 is stainless steel.

At least one cutting element 34 may be provided on the cutting assembly 34. The cutting element 34 may be positioned proximate the distal end of the cutting assembly 33. In certain embodiments, the cutting element 34 may include a main cutter portion 60 and at least one cutter extension portion 61 that extends from the main cutter portion 60.

In certain embodiments, the sacroiliac fusion system may include multiple undercutting systems 10. Each of the undercutting systems 10 may include a main cutter portion 60 having a different height and be mounted on different sides of the cutting assembly 33. Using such a configuration, the undercutting system 10 can be alternatively used at different stages of the process.

One such undercutting system 10 includes the main cutter portion 60 on the side of the cutting assembly 33 that is oriented towards the ilium after the cutting assembly 33 is deployed from the insertion apparatus 30. Another such undercutting system 10 includes the main cutter portion 60 on the side of the cutting assembly 33 that is oriented towards the sacrum after the cutting assembly 33 is deployed from the insertion apparatus 30.

Still another undercutting system 10 includes the main cutter portion 60 that extends from opposite sides of the cutting assembly 33 such that the main cutter portions 60 are oriented towards the sacrum and the ilium after the cutting assembly 33 is deployed from the insertion apparatus 30.

The main cutter portion 60 may have a height that is greater than the height of the cutting assembly 34. The main cutter portion 60 thereby enables a region between the ilium 14 and the sacrum 16 having a greater thickness to be prepared.

The main cutter portion 60 may have a height that is no greater than the corresponding pocket in the cap 90. Forming the main cutter portion 60 with such a configuration enables the cutting assembly 33 to be positioned substantially within a profile of the elongated shaft 40 when the cutting assembly 33 is in a retracted configuration so that the cutting assembly 33 does not interfere with the insertion of the distal end of the undercutting system 10 extending through the aperture 20 in the ilium 14.

The main cutter portion 60 may have a height of between about 1 millimeter and about 3 millimeters. In certain embodiments, the main cutter portion 60 may have a width of about 2 millimeters.

Similarly, the main cutter portion 60 may have a width that is no greater than an inner diameter of the elongated shaft 40. Forming the main cutter portion 60 with such a configuration enables the cutting assembly 33 to be positioned substantially within a profile of the elongated shaft 40 when the cutting assembly 33 is in a retracted configuration so that the cutting assembly 33 does not interfere with the insertion of the distal end of the undercutting system 10 extending through the aperture 20 in the ilium 14.

The main cutter portion 60 may have a width of between about 2 millimeters and about 5 millimeters. In certain embodiments, the main cutter portion 60 may have a width of about 3 millimeters.

The main cutter portion 60 may be curved proximate each of the corners thereof. Using the curved corners reduces the potential of the main cutter portion 60 digging too deeply into the surface of the ilium 14 or the sacrum 16 while the cutting assembly 33 is rotated.

In other embodiments, where it is desired to enhance the cutting ability of the cutting assembly 33, the main cutter portion 60 may be formed with sharp corners and at least a portion of the surface of the corners may be sharpened to enhance the cutting ability of the main cutter portion 60.

The main cutter portion 60 has a distal edge and a proximal edge that are disposed at opposite ends thereof. In certain embodiments, the distal edge and the proximal edge may be sufficiently sharp to cut through the tissue between the ilium 14 and the sacrum 16 that comes into contact with at least one of the distal edge and the proximal edge.

Alternatively, at least one of the distal edge and the proximal edge may include a cutting surface. In certain embodiments, cutting surfaces are provided on both distal and proximal edges of the main cutter portion 60. Providing the cutting surfaces on the distal and proximal edges enhances the ability of the main cutter portion 60 to cut through tissue between the ilium 14 and the sacrum 16 as the cutting assembly 33 is rotated.

As an alternative to or in addition to sharpening the main cutter portion 60, an abrasive surface may be provided on at least a portion of the outer surface of the main cutter portion 60. Examples of the abrasive surface include chemical etching and sintering material such as beads on the main cutter portion 60. Alternatively or additionally, the main cutting portion 60 may have a plurality of bristles extending therefrom.

The cutter extension portion 61 may have a generally planar configuration that extends from at least one of the upper and lower surfaces of the main cutter portion 60. While not illustrated, it is also possible for at least one of the cutter extension portions 61 to be positioned on the side surfaces of the main cutter portion 60.

In certain embodiments, the cutter extension portion 61 may extend in substantially equal distances on opposite sides of the main cutter portion 60. The cutter extension portion 61 may have a generally rectangular shape that is defined by a distal edge and a pair of side edges.

While it is illustrated that a height of the cutter extension portion 61 is approximately equal on opposite sides of the main cutter portion 60, it is possible to configure the cutter extension portion 61 so that the height of the cutter extension portion 61 is not approximately equal on opposite sides of the main cutter portion 60. Such a configuration may be used to preferentially cut one of the ilium 14 and the sacrum 16.

The height of the distal edge may be limited by the inner diameter of the elongated shaft 40 so that the cutting element 34 may be retracted within the insertion apparatus 30 when the insertion apparatus 30 is inserted into and removed from the region between the ilium 14 and the sacrum 16.

In certain embodiments, the height of the cutter extension portion 61 on opposite sides of the main cutter portion 60 is between about 1 millimeter and about 5 millimeters. In other embodiments, the height of the cutter extension portion 61 on opposite sides of the main cutter portion 60 is about 3 millimeters.

In certain embodiments, a width of the cutter extension portion 61 is approximately the same on opposite sides of the main cutter portion 60. The width of the cutter extension portion 61 may be between about 1 millimeter and about 5 millimeters. In other embodiments, the width of the cutter extension portion 61 is about 3 millimeters.

Corners proximate the intersection of the distal edge and each of the side edges may be curved. While such curvature could reduce the cutting ability of the cutter extension portion 61 that could be attained if the distal edge and the side edge intersected at a corner, this curvature may reduce the tendency of the cutter extension portion 61 to dig too deeply into the surfaces of the ilium 14 and the sacrum 16. As a result of this configuration, the cutter extension portion 61 would preferentially cut into the tissue between the ilium 14 and the sacrum 16 as opposed to cutting the ilium 14 and the sacrum 16.

While it is illustrated that the cutter extension portion 61 has a substantially equal thickness, it is possible for the thickness of the cutter extension portion 61 to vary. In certain embodiments, the thickness of the cutter extension portion 61 may be greater proximate to the main cutter portion 60 to resist bending or deformation of the cutting element 34.

In certain embodiments, a thickness of the cutter extension portion 61 may be between about 0.2 millimeters and about 2 millimeters. In other embodiments, the thickness of the cutter extension portion 61 may be about 0.5 millimeters.

While it is illustrated that the thickness of the cutter extension portion 61 is approximately equal on opposite sides of the main cutter portion 60, it is possible to configure the cutter extension portion 61 so that the thickness of the cutter extension portion 61 is not approximately equal on opposite sides of the main cutter portion 60.

The edge of the cutter extension portion 61 proximate the distal ends thereof may be sufficient to cut through the tissue between the ilium 14 and the sacrum 16. Using the cutter extension portion 61 without the sharpened edges may reduce a tendency of the cutter extension portion 61 to cut too deeply into the ilium 14 and the sacrum 16 while the cutting assembly 33 is rotated.

Alternatively, the edge of the cutter extension portion 61 proximate the distal ends thereof may be sharpened to facilitate cutting of tissue proximate the surfaces of the ilium 14 and the sacrum 16 while the cutting assembly 33 is rotated.

As an alternative to or in addition to sharpening the cutter extension portion 61, an abrasive surface may be provided on at least a portion of the outer surface of the cutter extension portion 61. Examples of the abrasive surface include chemical etching and sintering material such as beads on the cutter extension portion 61. Alternatively or additionally, the cutter extension portion 60 may have a plurality of bristles extending therefrom.

The cutter extension portion 61 may be oriented generally parallel to the length of the cutting element 34. In other embodiments, the cutter extension portion 61 may be oriented at an angle of between about 0 degrees and about 60 degrees with respect to a length of the cutting element 134. In other embodiments, the angle between the cutter extension portion 61 and the main cutter portion 60 may be about 30 degrees.

Orienting the cutter extension portion 61 at the angle with respect to the length of the main cutter portion 60 causes one of the edges to be disposed forwardly. Such a configuration may increase the ability of the cutting element 34 to cut tissue from between the ilium 14 and the sacrum 16 as the cutting assembly 33 is rotated.

While it is illustrated that the cutter extension portion 61 is oriented generally transverse to the surface of the main cutter portion 60, it is possible for the cutter extension portion 61 to be oriented at an angle with respect to the surface of the main cutter portion 60. For example, the cutter extension portion 61 may be oriented at an angle of between about 30 degrees and 60 degrees towards either a distal end or a proximal end of the cutting assembly 33. Using such a configuration enables the cutter extension portion 61 to also cut by scraping into the tissue.

While it is possible for the cutting element 34 to be placed at the distal end of the cutting assembly 33, in certain embodiments, the cutting element 34 may be mounted a distance from the distal end of the cutting assembly 33. Mounting the cutting element 34 a distance from the distal end of the cutting assembly 33 enables the cutting assembly 33 to define a path through the tissue between the ilium 14 and the sacrum 16, as opposed to the cutting element 34 being the primary component that defines the path through the tissue between the ilium 14 and the sacrum 16.

The cutter extension portion 61 may be positioned at a location that is approximately intermediate between the side edges of the main cutter portion 60. Placing the cutter extension portion 61 in this location may reduce twisting of the cutting assembly 33, which could potentially occur if the cutter extension portion 61 was located closer to one of the side edges of the main cutter portion 60.

The cutting element 34 having the preceding shape and characteristics may be formed from a variety of materials. A person of skill in the art will appreciate that the material used to fabricate the cutting element 34 should be suitable for use within a human body. An example of one such material for fabricating the cutting element 34 is stainless steel.

In certain embodiments, the cutting assembly 33 may be fabricated separately from the cutting element 34. Forming the structure in this manner enables different materials to be used for fabricating the cutting assembly 33 and the cutting element 34 so that the respective materials may be optimized based upon the function of the associated structure.

The cutting element 34 may be attached to the cutting assembly 33 using a variety of techniques that cause the cutting element 34 to be fixedly attached to the cutting assembly 33. One such suitable technique for attaching the cutting element 34 to the cutting assembly 33 is welding.

Alternatively, it is possible to fabricate the cutting assembly 33 and the cutting element 34 as a single unit such as by machining a block to provide a substantially flat cutting assembly 33 and a cutting element 34 that extends from the cutting assembly 33.

The undercutting system 10 may include a plurality of cutting assemblies 33 with cutting elements 34 having different distances heights. One of the cutting assemblies 33 with the cutting element 34 having the smallest height may be initially used. Thereafter, cutting assemblies 33 with cutting elements 34 having progressively larger heights may be used to form a progressively higher region between the ilium and the sacrum.

In addition to or in an alternative to forming the cutting elements 34 with different thicknesses, it is possible to use a series of cutting elements 34 to facilitate preparing the surfaces of the ilium 14 and the sacrum 16 in a predictable manner. In one such configuration, there is a series of three cutting elements 34 used to prepare the region between the ilium 14 and the sacrum 16.

The different cutting elements 34 can be part of a separate undercutting system 10 such as described above. Alternatively, the different cutting elements 34 to be alternatively connected to the insertion apparatus 30

The first cutting element 34 may be configured to preferentially cut tissue on the ilial side of the first cutting element 34. The first cutting element 34 may have one extension portion 61 that is positioned on the ilial side of the first cutting element 34.

The cutter extension portion 61 may have a first height that extends above a surface thereof. In certain embodiments, the cutter extension portion 61 may have a height of about 0.5 millimeters. The overall height of the first cutting element 34 is thereby about 2.5 millimeters.

Because the cutter extension portion 61 is on the ilial side of the first cutting element 34, this configuration may exhibit beneficial performance characteristics because this configuration accounts for the fact that a surface of the ilium 14 is harder than a surface of the sacrum 16.

The second cutting element 34 may also include one cutter extension portion 61 that is positioned on the sacral side of the first cutting element 34. The cutter extension portion 61 on the second cutting element 34 may have a height that is greater than the height of the cutter extension portion 61 on the first cutting element 34.

The cutter extension portion 61 may have a second height that extends above a surface thereof. In certain embodiments, the cutter extension portion 61 may have a height of about 0.5 millimeters. The overall height of the first cutting element 34 is thereby about 2.5 millimeters.

The configuration of the second cutting element 34 thereby enables an increased distance area between the ilium 14 and the sacrum 16 to be prepared, as compared to the first cutting element 34. However, similar to the first cutting element 34, the second cutting element 34 preferentially cuts on the ilial side of the second cutting element 34.

The third cutting element 34 may have an extension portion 61 that is positioned on the ilial and sacral sides thereof. While it is possible for the extension portions 61 to have different heights, in certain embodiments, the extension portions 61 each have a height of about 1 millimeter. The overall height of the third cutting element 34 is thereby about 4 millimeters.

Because the extension portions 61 are positioned on the ilial and sacral sides of the third cutting element 34, the third cutting element cuts tissue that is located on the ilial and sacral side of the third cutting element 34.

The cutting assembly 33 may be operably attached to the insertion apparatus 30 to facilitate extension and retraction of the cutting assembly 33 with respect to the insertion apparatus 30. In one embodiment, a control is provided for movement of the cutting assembly 33 that is separate from the control knob 46 used to move the probe assembly 32.

The cutting assembly control may be a knob 76 that is mounted to the insertion apparatus. Similar to the control knob 46, rotation of the cutting assembly control knob 76 in a first direction may cause extension of the cutting assembly 33 from the insertion apparatus 30 and rotation of the cutting assembly control knob 76 in a second direction may cause retraction of the cutting assembly 33 into the insertion apparatus 30.

In another embodiment, the probe assembly 32 and the cutting assembly 33 are both operably connected to the control knob 46. When the control knob 46 is initially rotated, the probe assembly 32 is extended progressively further from the insertion apparatus 30. Once the probe assembly 32 reaches its maximum extension, continued rotation of the control knob 46 causes the cutting assembly 33 to be extended from the insertion apparatus 30.

The distal end of the probe assembly 32 extends beyond the distal end of the cutting assembly 33 when these components are extended from the distal end of the insertion apparatus 30. Using this configuration enables the probe assembly 32 to guide the cutting assembly 33 and thereby reduce the potential of the cutting assembly 33 digging too deeply into the ilium 14 or the sacrum 16.

Once the probe assembly 32 has been extended the maximum distance from the distal end of the insertion apparatus 30 and the insertion apparatus 30 has been rotated at least one full revolution so that the probe assembly 32 has caused the path between the ilium 14 and the sacrum 16 to be defined, it may be possible for the cutting assembly 33 to be fully extended so that the distal end of the cutting assembly 33 is at approximately the same distance from the distal end of the insertion apparatus 30 as the probe assembly 32.

When the surgical procedure is completed and it is desired to remove the undercutting system 10, the control knob 46 is rotated in an opposite direction. This rotation initially causes retraction of the cutting assembly 33.

Once the cutting assembly 33 is fully retracted, continued rotation of the control knob 46 causes the probe assembly 32 to be retracted. After both the probe assembly 32 and the cutting assembly 33 are fully retracted within the insertion apparatus 30, the undercutting system 10 may be removed from the patient.

Using the probe assembly 32 in conjunction with the cutting assembly 33 enables the region between the ilium 14 and the sacrum 16 to be prepared for the sacroiliac fusion while minimizing the cutting assembly 33 digging too deeply into the surface of the ilium 14 or the sacrum 16.

While it is desirable to prepare the surfaces of the ilium 14 and the sacrum 16 by exposing bleeding bone, it is desirable to avoid the cutting assembly 33 digging into the surface of the ilium 14 or the sacrum 16 too deeply. When the cutting assembly 33 digs too deeply into the surface of the ilium 14 or the sacrum 16, it becomes more difficult to rotate the cutting assembly 33 because the ilium 14 and the sacrum 16 are much harder than the tissue located between the ilium 14 and the sacrum 16. The cutting assembly 33 having the characteristics set forth above meets these criteria.

To minimize the potential of the cutting assembly 33 breaking during the cutting process, a clutch mechanism may be provided between the handle and the cutting assembly 33. The clutch mechanism causes the operable connection between the handle 42 and the cutting assembly 33 to release when greater than a threshold force is encountered. When this occurs, the handle 42 rotates with respect to the cutting assembly 33.

An audible notification may be provided to indicate to the person using the undercutting system 10 that the clutch has been engaged. An example of which such audible notification is a scratching or clicking sound that is sufficiently loud to be heard outside of the patient.

After the clutch has been activated, the person operating the cutting assembly 33 may rotate the cutting assembly 33 in an opposite direction or partially retract the cutting assembly 33. Thereafter, the cutting process may be resumed.

Another configuration of the cutting assembly does not include a kerfed tube that extends over a probe assembly as described above. Rather, the cutting assembly utilizes a multiple strip design.

The multiple strip cutting assembly may include a central strip that is fabricated from a flexible material such as nitinol or stainless steel. The central strip may be similar to the probe assembly discussed above. An outer strip is attached to at least one surface of the central strip. In certain embodiments, the outer strip is attached to both sides of the central strip.

The outer strip may have a width that is similar to the width of the central strip. In other embodiments, the outer strip may have a width that is greater than or less than the width of the central strip.

The outer strips may be formed from a material that is different than the material from which the central strip is fabricated. In certain embodiments, the outer strips are fabricated from a more rigid material than the material that is used to fabricate the central strip. Forming the outer strips from a more rigid material than the central strip may enhance the cutting ability of the cutting assembly produced according to this embodiment. In certain embodiments, the outer strips are fabricated from stainless steel.

The outer strips are attached to the central strip so that the central strip and the outer strips move as a unit. Alternatively, the outer strips may move together and the inner strip may move independently, as with the independent operation of the probe assembly 32 and cutting assembly 33 described above. An example of one technique that may be used to attach the outer strips to the central strip is welding.

At least one cutting element may extend from each of the outer strips. The cutting element may have a similar configuration to the cutting elements that are used in conjunction with the cutting assembly illustrated in FIGS. 1-5.

As an alternative to or in addition to the cutting elements, an abrasive surface may be provided on at least a portion of the outer surface of the cutting elements. Examples of the abrasive surface include chemical etching and sintering material such as beads on the cutting elements. In still other configurations, the cutting elements may include a plurality of bristles extending therefrom.

An advantage of the preceding configuration is that the cutting assembly has reduced complexity compared to the cutting assembly utilizing the kerfed tube. Additionally, this configuration does not include stress concentration points that are present where the kerfs are cut into the tube of the cutting assembly illustrated in FIGS. 6-7.

A disadvantage of the preceding configuration is that the cutting assembly has a reduced ability to carry cut tissue that enters the kerfs. Additionally, there is no incidental scratching of tissue with the kerfed region, which enhances the cutting performance.

As a preliminary step in the use of the undercutting system 10 in conjunction with performing a sacroiliac fusion, the undercutting system 10 is sterilized. In certain embodiments, the sterilization is performed using steam. Prior to placing the undercutting system 10 in the steam sterilization unit, the probe assembly 32 and the cutting assembly 33 are moved to the extended position.

If the probe assembly 32 and the cutting assembly 33 are in the retracted position during the steam sterilization process, the heat associated with the steam may cause the distal ends of the probe assembly 32 and/or the cutting assembly 33 to become heat set.

Having the distal ends of the probe assembly 32 and the cutting assembly 33 become heat set is undesirable because the distal ends of the probe assembly 32 and the cutting assembly 33 would move in a curved path while performing the undercutting procedure, which corresponds to the heat set curvature as opposed to tracking in a generally linear direction between the ilium 14 and the sacrum 16.

To facilitate use of the undercutting system 10 and the performance of the sacroiliac fusion, the patient on which the sacroiliac fusion is to be performed may be positioned in a prone or supine orientation on an operating room table or other support structure that is used in conjunction with this procedure.

While it is possible to form a relatively large incision and then pull back the tissue between the skin and the ilium so that the surface of the ilium could directly be viewed when using the undercutting system 10 of the invention, such a process could cause more damage to the tissue between the skin and the ilium, which could increase the time for the patient to recover from the surgical procedure.

The tissue penetrated when using the method discussed herein may include (when moving from lateral to medial)—skin, gluteus maximus, gluteus medius, gluteus minimus, lateral ilium cortex, medial ilium cortex, sacroiliac joint cartilage (ilium and sacrum), lateral sacral cortex, sacral ala, sacral vestibule (which is also known as alar root, sacral pedicle and sacral isthmus) and sacral vertebral body.

Other critical soft tissue that is proximate to where the undercutting system 10 is being used may include (when moving from lateral to medial)—superior cluneal nerves, superior gluteal artery and vein, L4, L5, S1 and S2 nerve roots, iliac artery, iliac vein, sacral forts also known as neuroforamina), bowels and sacral canal.

Additional relevant anatomical landmarks that have not been previously mentioned include greater sciatic notch, alar slope and iliac cortical density, sacral prominence, pubic symphysis, pelvic brim/arcuate line and S1 end plate.

A variety of techniques may be used to determine the location at which the first aperture 20 and the second aperture 20 are to be formed in the ilium as well as the orientation of the ilium so that the first aperture 20 and the second aperture 20 may be in a desired position and not result in damage to the tissue adjacent to and/or above where the first aperture 20 and the second aperture 20 are to be formed.

A non-limiting example of a technique that may be used to determine the location and orientation of the first aperture 20 and second aperture 20 is a fluoroscope. To assist in evaluating the location and orientation of the anatomical structures proximate to where the undercutting system 10 will be used, it is possible to perform the fluoroscopic imaging from multiple directions.

One such direction for the fluoroscopic imaging is a lateral view across the patient's pelvis. The lateral sacral view provides a visualization of the starting point for the sacroiliac joint access by best showing critical boundaries of the safe bony corridor such as the anterior sacral cortex and the alar slope.

While less clear but also visible, the lateral sacral view provides the ability to see the sacral neural foramina and the spinal canal. The lateral view along with the outlet view can help to identify sacral dysmorphism, a challenging anatomical variation.

The lateral view may be obtained by aligning the projections of the two greater sciatic notches and the two iliac cortical densities. To minimize the x-ray exposure, it is not necessary for there to be exact alignment of the preceding elements.

If the greater sciatic notches and the iliac cortical densities are not simultaneously aligned, it is possible to split the difference between these components. Alternatively, when alignment of the iliac cortical densities is difficult, alignment of the greater sciatic notches may be sufficient for performing the lateral fluoroscopic image.

It should also be noted that when aligning for the lateral view, true lateral of the sacrum may not appear to be true lateral to the patient. For the purposes of this invention, the important facture is the alignment of the sacrum.

Another view for the fluoroscopic imaging is an anteroposterior view with a caudal tilt. This view, which is referred to as the inlet view, may provide an excellent mediolateral view of the advancing guide pin and/or bone screw. This view also best enables avoidance of the posterior spinal canal and the anterior limit of the sacrum.

The inlet view is used in conjunction with the outlet view, which is described below, while advancing the guide pin or bone screw medially into the patient. Together the inlet view and the outlet view provide orthogonal images to guide screw insertion in all three dimensions.

The inlet view is obtained by tilting the fluoroscopic receiver caudal from the anteroposterior position. The device is aligned with a line created by the anterior-inferior sacral cortex and the iliac pelvic brim with the second foramina. To minimize the x-ray exposure, it is not needed for there to be perfect alignment of the inlet view.

Still another view of the fluoroscope imaging is an anteroposterior view with a cephalad tilt. This view, which is referred to as the outlet view, may provide an excellent mediolateral view of the advancing guide pin and bone screw towards the center of the sacral body. The outlet view enables avoidance of the Superior S1 end-plate and the S1 neuroforamina.

The outlet view may be used in conjunction with the inlet view while advancing the guide pin or bone screw medially into the patient. When viewed together, the inlet view and the outlet view provide nearly orthogonal image to guide screw insertion in all three dimensions.

The outlet view is best suited for viewing the sacroiliac joint to facilitate cartilage excision. While the outlet view may be similar to a "Judet" view, it is distinct from such a view and, as such, these views are not interchangeable.

The outlet view can be used to assure that the tip of the guide pin is cephalad to the sacral nerve foramen. The outlet view also distinguishes the cephalad border of the sacrum, which is actually the posterior sacral alar region. The anterior aspects of the sacral ala are sloped inferiorly relative to the posterior sacral alar region. The failure to account for this forward sloping could result in the extraosseus instrument or screw placement being dangerously close to the iliac vessels and/or the fifth lumbar nerve root.

The outlet view may be obtained by tilting the fluoroscope receiver cephalad from an anteroposterior position until the top of the symphysis pubis is located at the S2 body. To minimize x-ray exposure, it is not needed for there to be perfect alignment of the outlet view.

As an initial point in locating a location for access, a relatively small guide pin such as having a length of about 3 millimeters is held to the outside of the patient proximate to the location of the iliosacral corridor. The tip of the guide pin may be positioned caudal to the iliac cortical density and cephalad to the interosseous path of the upper sacral nerve root.

The lateral projection of the iliosacral corridor identifies the safest position for the distal end of the bone screw that is inserted laterally. The proximal entry point may be outside the iliosacral corridor.

The guide pin tip can be located within the midportion of the alar bone on the lateral image. The iliosacral corridor is the best location for passage of the bone screw using in conjunction with the sacroiliac fusion.

After marking the skin, a vertical incision having a length of between about 2 and 4 centimeters is formed in the skin. Next, using blunt dilation, a probe is extended through the tissue in line with the future path of the screw until reaching the ilium bone.

The most effective area for joint preparation may be the inferior-anterior edge of the safe zone closer to the articular cartilage portion of the joint as opposed to the interosseous portion directly lateral of the safe zone.

The articular portion of the joint is more flat, which is advantageous to encourage fusion at the articular portion of the sacroiliac joint. In contrast, the interosseous portion of the joint, which is posterior to the safe zone, is steeply angulated from perpendicular, and very lumpy and irregular.

After appropriate preparation of the patient and identification of the location for the sacroiliac fusion, at least one aperture 20 is drilled through the ilium 14. This aperture 20 may also at least partially extend into the sacrum 16, as illustrated in FIG. 10. In certain embodiments, there are three apertures drilled.

Even though FIG. 10 illustrates that the procedure is performed by initially drilling into the ilium 14, it is also possible to perform the sacroiliac fusion by initially drilling into the sacrum 16. In certain circumstances, it may present fewer challenges in gaining access for the sacroiliac fusion by initially drilling into the ilium 14.

A conventional surgical drill 92 and drill bit 94 may be utilized to form the aperture 20. The aperture 20 may be formed with a diameter that is selected based upon a diameter of the insertion apparatus 30 that will be inserted into the aperture 20 as part of the undercutting process.

As illustrated in FIG. 10, the drill 92 may be oriented generally transverse to a surface of at least one of the ilium 14 and the sacrum 16 proximate to where the aperture 20 is being formed. A person of skill in the art will appreciate that neither the ilium 14 nor the sacrum 16 are substantially flat. Additionally, the adjacent surfaces of the ilium 14 and the sacrum 16 may not be substantially parallel to each other proximate to where it is desired to form the aperture 20.

The aperture 20 may be oriented generally transverse to the ilium 14. As used herein, generally transverse means that an angle between the aperture 20 and the ilium 14 proximate to where the aperture 20 is formed is between about 45 degrees and about 90 degrees. In other embodiments, the angle is between about 60 degrees and about 90 degrees. The orientation of an inner surface of the ilium 14 is more important than the orientation of an outer surface of the ilium 14.

The apertures 20 may include a first aperture 20 that is used in conjunction with a first screw having a diameter of about 12.5 millimeters. In this situation, the drill bit used to form the first aperture 20 may have a diameter of approximately 9 millimeters.

The first aperture 20 may be formed across the sacroiliac joint at the S1 level. The first aperture 20 may be positioned to favor an anterior-inferior side of the sacroiliac joint. The first aperture 20 may be oriented at an angle so that the distal end of the first screw is slightly posterior and superior of a proximal end of the first screw.

The apertures 20 may also include a second aperture 20 that is used in conjunction with a second screw having a diameter of about 6.5 millimeters. In this situation, the drill bit used to form the second aperture 20 may have a diameter of approximately 4 millimeters.

The second aperture 20 may be formed across the sacroiliac joint proximate to where the first aperture 20 is formed in the sacroiliac joint. The second aperture 20 may be oriented at an angle so that the distal end of the second screw is slightly anterior and superior to a proximal end of the second screw.

Figure 11:
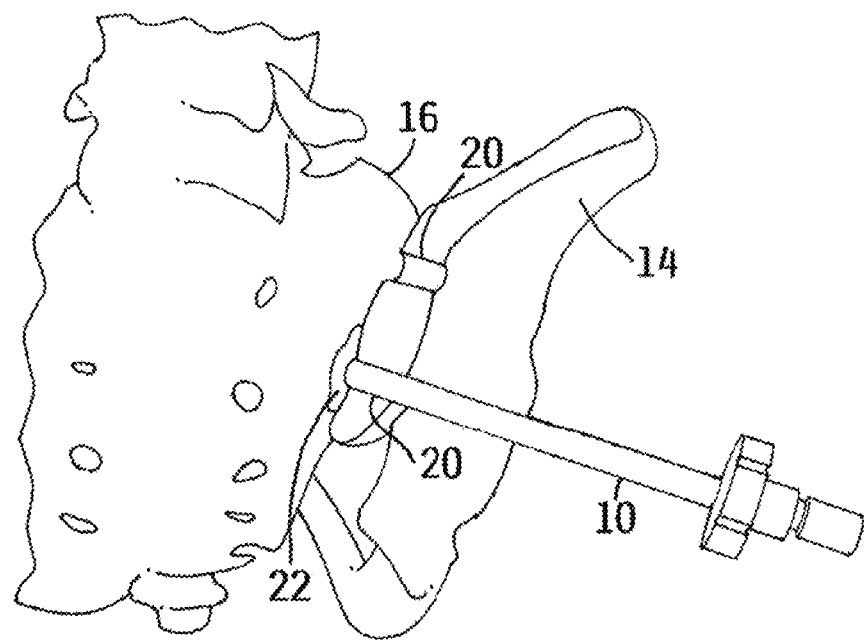
FIG. 11 is a partially cut away perspective view of an undercutting system being inserted into the aperture.

Next, the undercutting system 10 is positioned in a retracted configuration so that the probe assembly 32 does not interfere with the insertion process. The distal end of the undercutting system 10 is extended into the aperture 20, as illustrated in FIG. 11.

Figure 12:
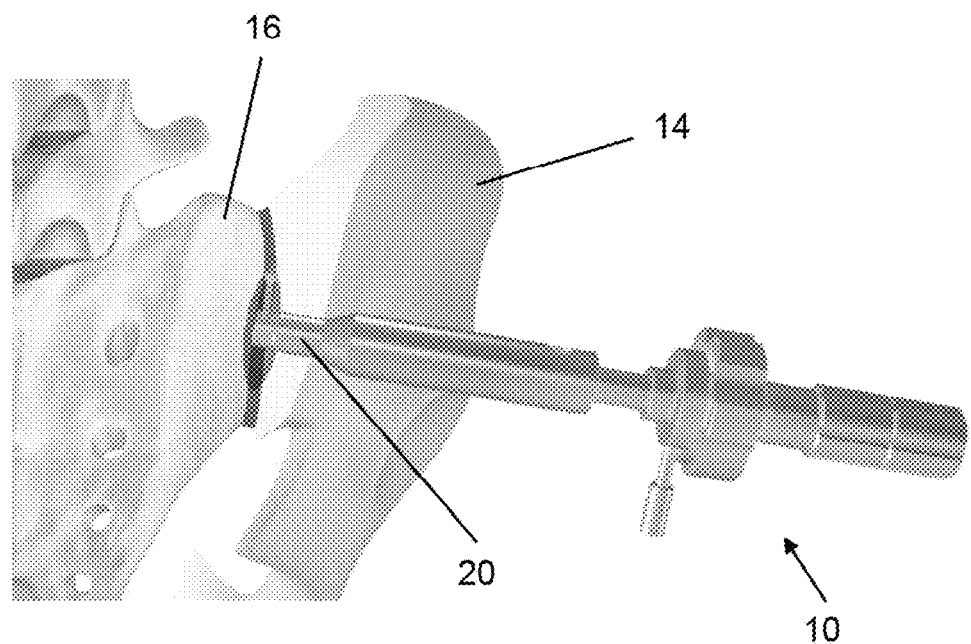
FIG. 12 is a partially cut away perspective view of the undercutting system being used to form an undercut region between the sacrum and the ilium.

Once the distal end of the undercutting system 10 is positioned between the ilium 14 and the sacrum 16, the probe assembly 32 is moved to an at least partially extended configuration, as illustrated in FIG. 12.

The undercutting system 10 is rotated to so that the probe assembly 32 causes a path to be defined between the ilium 14 and the sacrum 16. By defining the path using the probe assembly 32, the potential of the cutting assembly 33 digging too deeply into the ilium 14 or the sacrum 16 is reduced.

Next, the cutting assembly 33 is extended over the probe assembly 32 until the cutting element 34 extends from the distal end of the insertion apparatus 30 and is positioned between the ilium 14 and the sacrum 16. The undercutting system 10 is rotated so that the cutting element 34 contacts tissue between the ilium 14 and the sacrum 16 to cause such tissue to be cut into pieces.

Alternatively or additionally, the cutting element 34 may cause cartilage and/or tissue to be scraped from the surface of at least one of the ilium 14 and the sacrum 16. If it is desired to prepare a region having a larger diameter, the cutting assembly 33 may be advanced further and then the undercutting system 10 may be rotated.

Depending on a variety of factors such as the sharpness of the cutting assembly 33 and the hardness of the material being cut, it may not be possible to merely cut through the cartilage and bone using just a rotational motion. Rather, it may be necessary to alternate rotating the undercutting system 10 in clockwise and counter clockwise directions to increase the area that is prepared.

The control knob can be periodically rotated to cause the cutting assembly 33 to extend progressively further from the undercutting system 10. While in many circumstances, it may be desirable to prepare a circular area, it is also possible to use the concepts of the invention to prepare a portion of a circular area.

Alternatively or additionally, the probe assembly 32 may be withdrawn and a cutting assembly may be used to cut tissue in the region between the ilium 14 and the sacrum 16 that has been defined by the probe assembly 32.

Contact between the cutting assembly 33 and the inner surfaces of the ilium 14 and the sacrum 16 causes the respective surfaces to be abraded to create bleeding bone, which may be desirable to facilitate bone growth between the ilium 14 and the sacrum 16 as part of the sacroiliac fusion process.

A variety of techniques may be used to evaluate the amount of cartilage that has been removed and the extent to which the surfaces of the ilium and the sacrum have been prepared. Examples of such suitable techniques include monitoring the sound emitted during the cutting process, as the cutting of bone may make a scraping sound.

The person operating the undercutting system may monitor the performance of the process using the feel of the cutting head, as it may be more difficult for the cutting head to cut through the ilium and the sacrum than the cartilage.

It is also possible to monitor the progress of the preparation for the sacroiliac fusion using a fluoroscope. While these techniques are described individually, it is possible for one or more of the preceding techniques to be combined.

In certain embodiments, the bits of cartilage and other tissue from between the ilium 14 and the sacrum 16 may become caught in the cutting assembly 33 during the cutting process. In such a situation, the cartilage and other tissue are removed from between the ilium 14 and the sacrum 16 when the cutting assembly is retracted.

It may be necessary to clean the cutting assembly 33 and then reinsert the cutting assembly 33 into the region between the ilium 14 and the sacrum 16 to remove additional bits of the cartilage and other tissue.

Alternatively or additionally, a technique may be utilized to remove the bits of cartilage and other tissue from between the ilium 14 and the sacrum 16. One suitable apparatus that may be used for remove the bits of cartilage and other tissue is a radial deployment surgical tool, which is described in U.S. application Ser. No. 12/941,763, which was filed with the U.S. Patent & Trademark Office on Nov. 8, 2010, and which is assigned to the assignee of the present patent application.

Another technique for removing the cut up bits of cartilage is to flush the region with a fluid and then suction out the water with the cut up bits of cartilage. The process may be repeated until a desired amount of the cut up bits of cartilage is removed from between the ilium and the sacrum.

After the surfaces of the ilium and the sacrum have been prepared, a bone graft may be inserted. Then, a variety of techniques may be used to maintain the ilium and the sacrum in a fixed position with respect to each other. Examples of suitable fixation techniques include bone screws, cannulated screws, pins, cages, glue, coupled device with ball and socket and Herbert screws.

Figure 13:
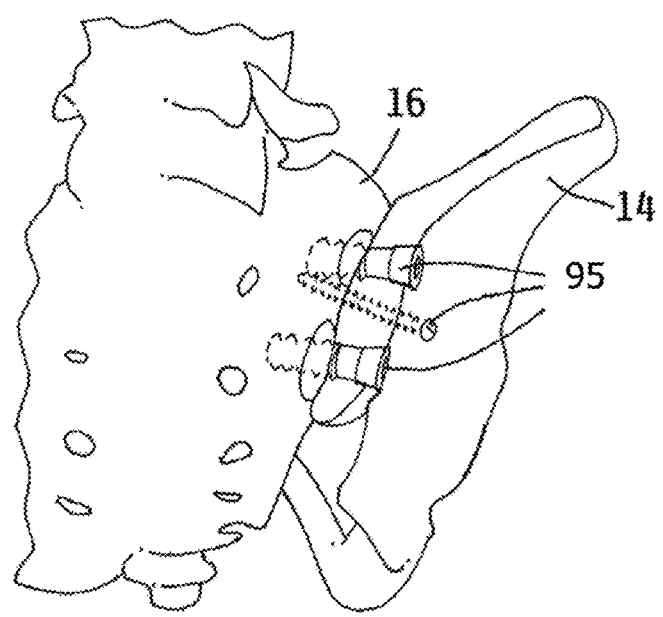
FIG. 13 is a partially cut away perspective view of fasteners inserted into the apertures.
Figure 14:
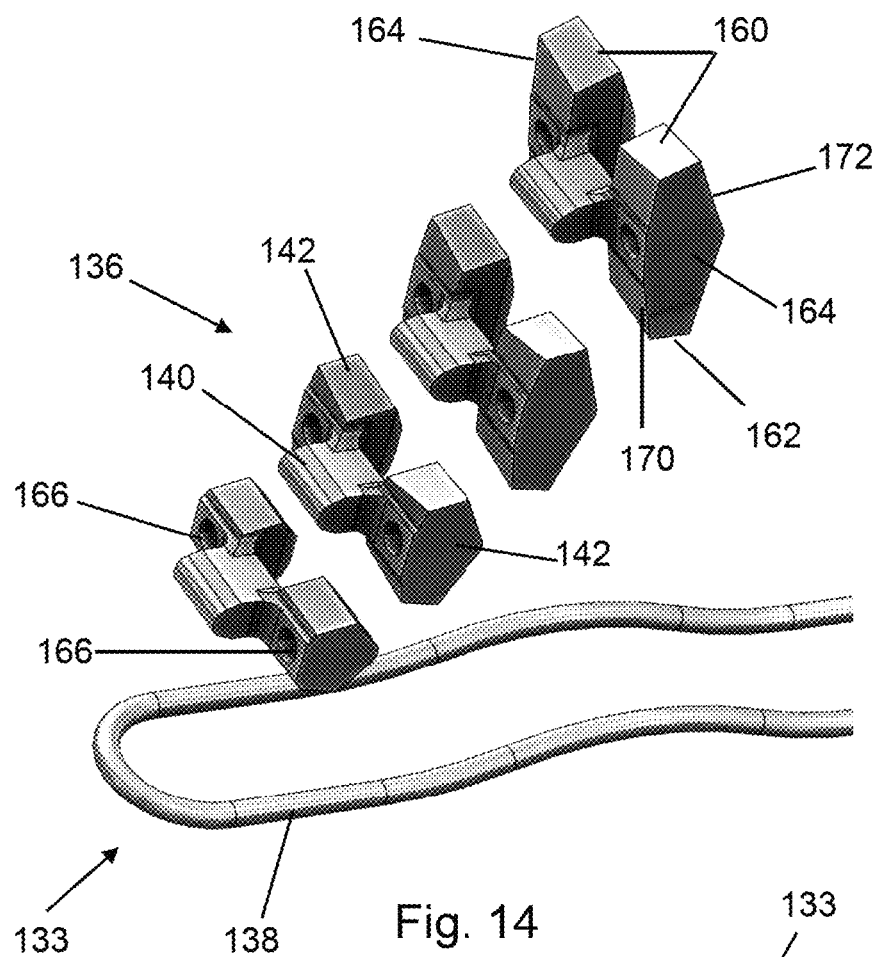
FIG. 14 is an exploded perspective view of an alternative configuration of the cutting assembly.
Figure 15:
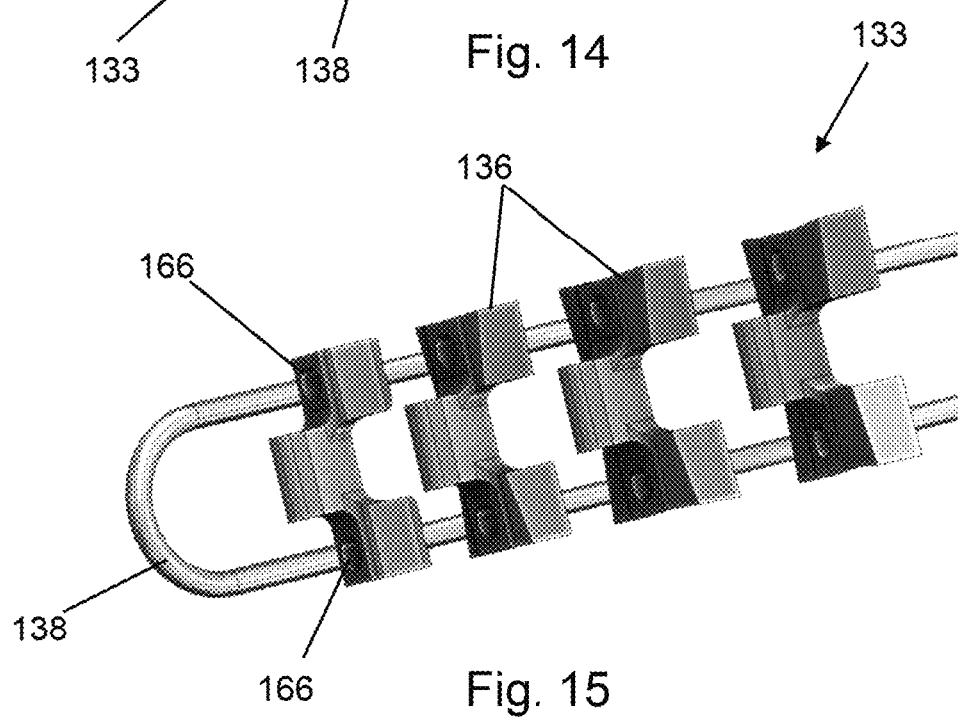
FIG. 15 is a partially assembled perspective view of the cutting assembly of FIG. 14.

Thereafter, bone screws 95 may be inserted into each of the apertures 20, as illustrated in FIG. 13. The bone screws 95 will be effective at maintaining the ilium 14 and the sacrum 16 in a stationary position with respect to each other as bone grows between the ilium 14 and the sacrum 16 to cause fusion of the ilium 14 and the sacrum 16.

In certain embodiments, the orientation of each of the apertures 20 may be generally parallel to each other. In other embodiments, the apertures 20 may be formed in a non-parallel relationship. In certain embodiments, in addition to the aperture that is prepared with the undercutting system, one or more additional apertures may be formed on which the undercutting system is not used. These additional apertures may have a smaller diameter than the apertures in which the undercutting system is used.

For example, the two screws 95 on each side converge toward the safe zone as illustrated in FIG. 13, which are lateral, inlet and outlet fluoroscopic images of the pelvis region. It is to be noted that neither of the bone screws 95 penetrate into the alar scope, which could be caused by the entry point being too cephalad. Such a situation is to be avoided because it can result in complications to the patient, which requires immediate correction.

While the figures only illustrated the procedure being performed on one side of the patient, a person of skill in the art will appreciate that the process may be repeated on the other side of the patient.

While the concepts of the invention are primarily described in conjunction with preparation for a sacroiliac fusion, a person of skill in the art will appreciate that the concepts may be adapted for other joints in the body. The concepts may also be used for preparing an interior region of a bone.

As an alternative to disturbing the surfaces of the ilium 14 and the sacrum 16 to expose bleeding bone, it is possible for the undercutting system to remove more bone from at least one of the ilium 14 and the sacrum 16. Such a process could create a relatively planar prepared region between the ilium 14 and the sacrum 16. Because the ilium 14 and the sacrum 16 are not substantially flat, a greater amount of bone may be removed using such a process. This process obliterates a portion of at least one of the ilium 14 and the sacrum 16.

However, when performing such a process, care should be exercised so that the cutting assembly does not cut all the way through the ilium 14 or the sacrum 16. Additionally, care should be exercised to not remove too much of the ilium 14 or the sacrum 16 as such a process could result in weakening a portion of the ilium 14 or the sacrum 16 into which the fastening device is affixed.

The process associated with this embodiment may require the use of a sharper and/or stronger cutting assembly 33 so that the cutting assembly 33 resists damage when forces needed to cut more deeply into the ilium 14 and sacrum 16 are used.

After the fusion region is prepared, the cut up bone, cartilage and other tissue may be removed from the fusion region using one of the processes described in the other portions of this patent application. A bone growth material may be placed into the fusion region. A bone screw or other fastening device may be used to retain the ilium 14 and the sacrum 16 in a stationary position with respect to each other while bone grows between the ilium 14 and the sacrum 16.

An alternative embodiment of the undercutting system 110, which is illustrated in FIGS. 14-17, includes a cutting assembly 133 having a plurality of cutting elements 136 that are mounted with respect to a support wire 138.

The cutting elements 136 include a central section 140 and two wing sections 142 on opposite sides of the central section 140. The central section 140 extends towards a distal end of the cutting assembly 133 and the wing sections 142 extend toward the proximal end of the cutting assembly 133.

The central section 140 has a width that is approximately the same as a distance between the wing section 142. When the cutting elements 136 are placed in an adjacent relationship, the central section 140 extends between the wing sections 142 on an adjacent cutting element 136.

This configuration causes the cutting elements 136 to resist lateral movement with respect to each other as the undercutting system 110 is rotated. This configuration also reduces lateral pivoting of the adjacent cutting elements 136 with respect to each other.

In certain embodiments, a distal end 144 of the central section 140 on a first cutting element 136 is adjacent to a proximal end 146 of the central section 140 on a second cutting element 136 that is adjacent to the first cutting element 136. This configuration also reduces lateral pivoting of the adjacent cutting elements 136 with respect to each other.

Figure 17:
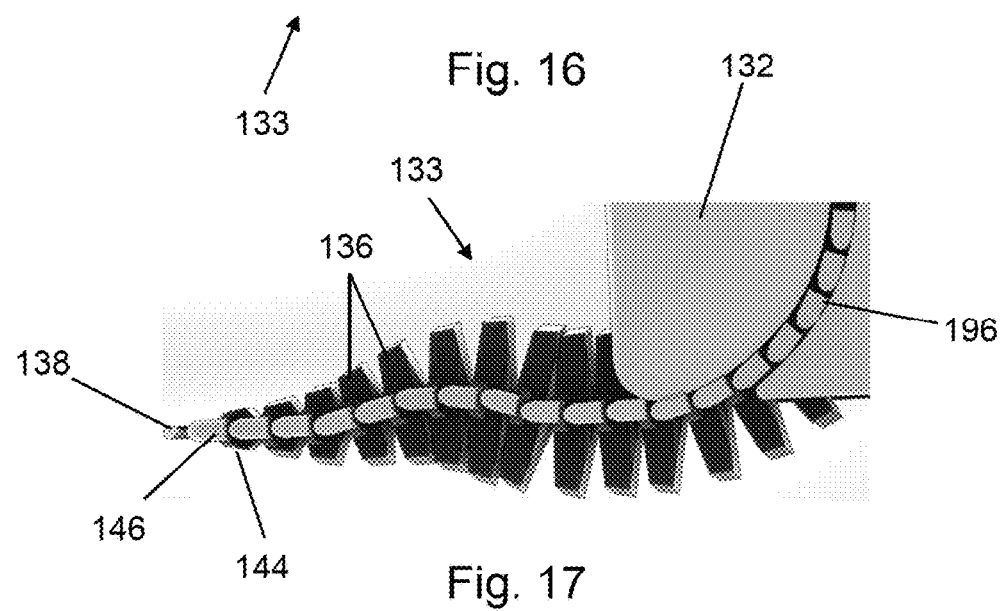
FIG. 17 is a sectional view of the cutting assembly of FIG. 14 extending from an insertion apparatus.

As illustrated in FIG. 17, the distal end 144 of the central section 140 may be curved to facilitate vertical pivoting of the adjacent cutting elements 136 with respect to each other. While not illustrated, it is possible for the proximal end 146 of the central section 140 to also be curved.

The central section 140 has a height that is less than the height of the wing sections 142. The height of the central sections 140 may be substantially the same on all of the cutting elements 136.

In certain embodiments, the two wing sections 142 on each cutting element 136 may be shaped substantially similar to each other. Each wing section 142 has an upper surface 160 and a lower surface 162. The upper surface 160 and the lower surface 162 may both be in a substantially horizontal orientation. In other embodiments, the upper surface 160 and the lower surface 162 may be oriented at an angle to enhance the ability of the cutting elements 136 to cut through tissue and/or bone during use.

The wing sections 142 also include side surfaces 164 on the side of the wing section 142 that is opposite the central section 140. The side surfaces 164 may be in a generally vertical orientation. The wing sections 142 may each have a similar width so that when cutting elements 136 are positioned adjacent to each other, the side surfaces 164 are generally aligned with each other.

The wing sections 142 each include a distal surface 170 and a proximal surface 172. The distal surface 170 and the proximal surface 172 are each oriented in a generally vertical orientation.

At least one of the distal surface 170 and the proximal surface 172 may have a convex configuration. In certain embodiments, one of the distal surface 170 and the proximal surface 172 have a greater convex configuration.

An orientation of the convex configuration is between the upper surface 160 and the lower surface 162 such that intermediate the upper surface 160 and the lower surface 162, the cutting element 136 has the greatest width.

Each of the cutting elements 136 may have a similar smallest distance between the distal surface 170 and the proximal surface 172 and each of the cutting elements 136 may have a similar largest distance between the distal surface 170 and the proximal surface 172.

Because of this configuration, an angle between the upper surface 160 and the adjacent proximal surface 172 may be larger for the shorter cutting elements 136 than for the taller cutting elements 136. This configuration provides the distal end of the cutting assembly 133 with enhanced flexibility compared to the proximal end of the cutting assembly 133.

Using the convex configuration enhances the ability of adjacent cutting elements 136 to vertically pivot with respect to each other such as moving from a retracted configuration inside of the insertion apparatus 130 to an extended configuration between the ilium 14 and the sacrum 16. The convex configuration also facilitates pivoting of the cutting elements 136 with respect to each other when the cutting assembly 133 is rotated between the ilium 14 and the sacrum 16.

The wing sections 142 may be formed with different heights. Proximate the distal end of the cutting assembly 133, the wing sections 142 may have a smaller height as compared to the height of the wing sections 142 proximate the proximal end of the cutting assembly 133. Forming the wing sections 142 with the progressively larger height enables a greater thickness of tissue between the ilium 14 and the sacrum 16 to be prepared.

The wing sections 142 proximate distal end of the cutting assembly 133 may have a height of between about 2 millimeters and about 10 millimeters. In certain embodiments, the wing sections 142 proximate the distal end of the cutting assembly 133 have a height of about 4 millimeters.

The wing sections 142 proximate the proximal end of the cutting assembly 133 may have a height of between about 5 millimeters and about 15 millimeters. In certain embodiments, the wing sections 142 proximate the proximal end of the cutting assembly 133 have a height of about 9 millimeters.

On opposite sides of the central section 140, apertures 166 extend through each of the wing sections 142. The apertures 166 may be generally cylindrical and have a diameter that is slightly larger than the diameter of the support wire 138. Alternatively or additionally, an aperture may be formed through each of the central sections 140 and such apertures can receive the support wire 138.

The support wire 138 may be fabricated from a flexible material that facilitates repeated extension and retraction of the cutting assembly 133. In certain embodiments, the support wire 138 is fabricated from a metallic material such as nitinol.

Figure 16:
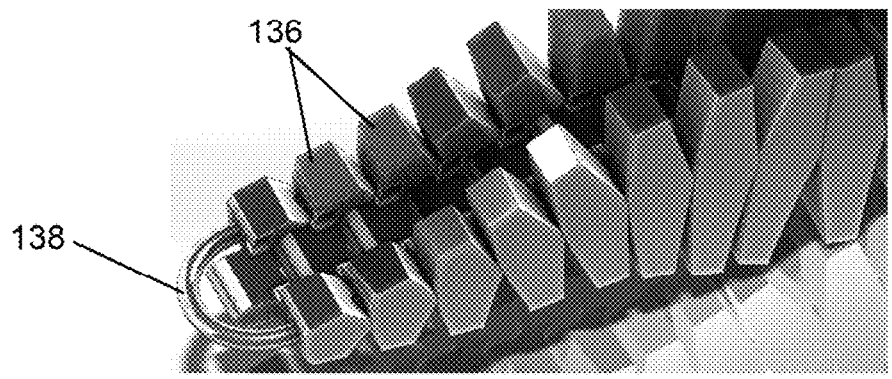
FIG. 16 is an assembled perspective view of the cutting assembly of FIG. 14.

When the cutting elements 136 are assembled over the support wire 138, as illustrated in FIG. 16, the cutting elements 136 are substantially adjacent to each other but pivotable with respect to each other, as illustrated in FIG. 17.

A lock mechanism may be used to retain the cutting elements 136 in an adjacent relationship. The lock mechanism thereby enhances the ability of the adjacent cutting elements 136 to impart force to each other.

The lock mechanism engages each end of the support wire 138 that extends through the most proximal cutting element 136. The lock mechanism can releasably engage the support wire 138. Such a configuration facilitates replacing the cutting elements 136 or the support wire 138 such as if the component is damaged.

As the undercutting system 10 rotates, the cutting assembly 133 can be configured to extend from the insertion apparatus 130. In certain embodiments, the rate at which the cutting assembly 133 extends from the insertion apparatus 130 is selected so that one additional cutting element 136 is advanced for each rotation of the undercutting system 10.

Figure 18:
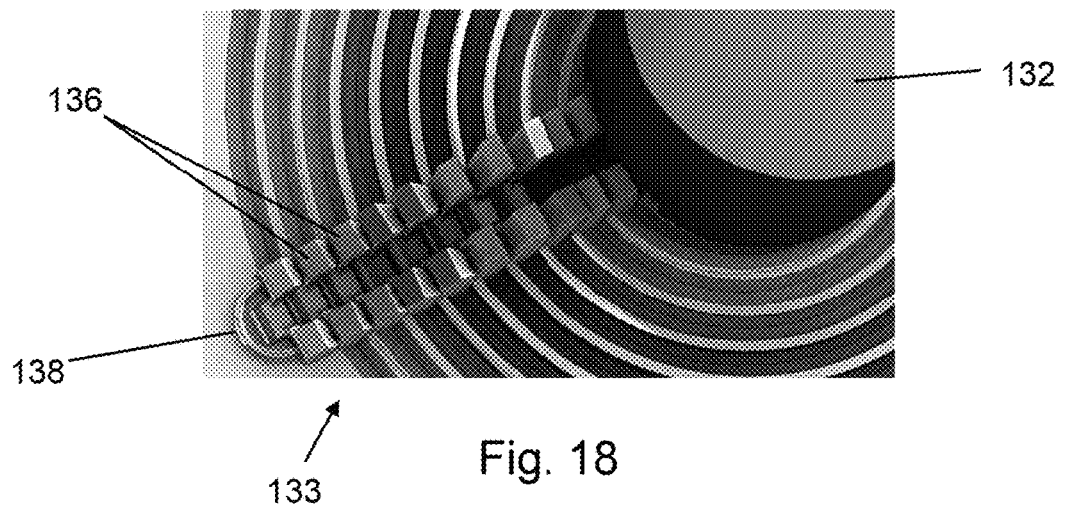
FIG. 18 is a top view of the cutting assembly of FIG. 14 used to form a plurality of grooves in a cutting process.
Figure 19:
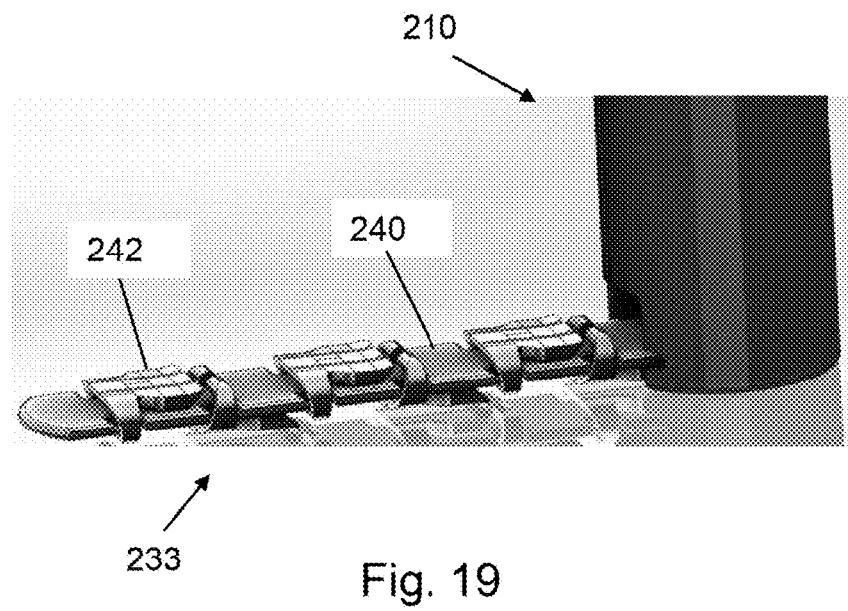
FIG. 19 is a perspective view of an alternative embodiment of the undercutting system in an insertion configuration.

Such a process produces a spiral cutting pattern, which is illustrated in FIG. 18. This process also facilitates cutting progressively deeper into the tissue as the cutting assembly 133 is advanced from the insertion apparatus 130.

The insertion apparatus 130 used in conjunction with this embodiment may have a similar configuration to the insertion apparatus 30 described above and illustrated in FIGS. 1-5. The insertion apparatus 130 may include a curved channel 196 that directs the cutting assembly 133 from an orientation that is generally aligned with a central axis of the insertion apparatus 30 to an orientation that is generally perpendicular to the central axis of the insertion apparatus 30.

In certain embodiments, the channel 196 may emerge from the insertion apparatus 130 on a lower surface of the insertion apparatus, as illustrated in FIG. 17. In such a configuration, the distal end of the insertion apparatus 130 should be positioned in a spaced-apart configuration from the sacrum 16 to provide sufficient space between the sacrum and the distal end of the insertion apparatus to permit extension of the cutting assembly 133 from the insertion apparatus 130.

The channel 196 may be formed with a profile that is similar to the profile of the cutting elements 136 that includes a central channel section and wing channel sections. The central channel section may be formed with a height and a width that are both slightly larger than the height and the width, respectively, of the central section 140. The wing channel sections are formed with a height and a width that are both slightly larger than the height and the width, respectively, of the largest wing section 142.

Forming the channel 196 with a size and shape that is similar to the size and shape of the cutting elements 136 minimizes the potential of the cut tissue entering the interior of the undercutting system 110 and thereby potentially interfering with the operation of the undercutting system 110.

Another embodiment of the undercutting system 210, which is illustrated in FIGS. 19-22, utilizes a linear cutting motion, in contrast to the rotational cutting motion utilized by the other configurations of the undercutting system that are described herein.

The cutting assembly 233 includes an elongated base 240 to which a plurality of cutting elements 242 are operably attached. The elongated base 240 may have a configuration that is similar to the probe assembly 32 that is described with respect to the configuration illustrated in FIGS. 1-5.

The elongated base 240 may be fabricated from a flexible material such as nitinol that enables the elongated base 240 to deflect from a retracted configuration inside of the insertion apparatus 230 in which the elongated base 240 is generally aligned with an axis of the insertion apparatus 240. When in the extended configuration, at least a distal portion of the elongated base 240 may be oriented in a direction that is generally perpendicular to the axis of the insertion apparatus 240.

The elongated base 240 may be fabricated from a single layer or from multiple layers. An advantage of fabricating the elongated base 240 from multiple thinner layers is that the multiple thinner layers may be more flexible than the thicker single layer.

A distal end of the elongated base 240 may be relatively thin to enhance the ability of the distal end to form a path through tissue that is between the ilium 14 and the sacrum 16. However, the distal end of the elongated base 240 should not be too sharp to cause the distal end to cut into the ilium 14 or the sacrum 16 as the cutting assembly 233 is being extended from the insertion apparatus 230.

In certain embodiments, the distal end of the elongated base 240 is rounded between the upper and lower surfaces of the elongated base 240 and is rounded between the opposite side surfaces of the elongated based 240.

The cutting elements 242 are operably attached to at least one side of the elongated base 240. In certain embodiments, the cutting elements 242 are attached to both sides of the elongated base 240. The cutting elements 242 may be attached in an alternating configuration such every other cutting element 242 is on an opposite side of the elongated base 240.

Figure 20:
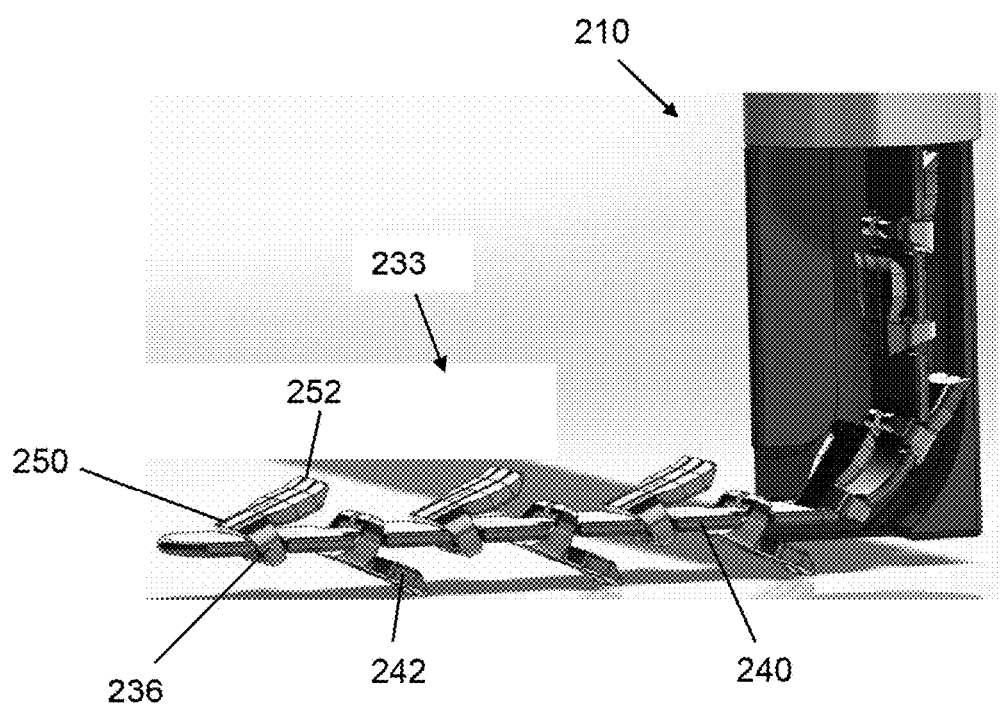
FIG. 20 is a perspective view of the undercutting system of FIG. 19 in a retraction configuration.

The cutting elements 242 are movable with respect to the retracted configuration (FIGS. 19 and 21) and an extended configuration (FIGS. 20 and 22). When the cutting elements 242 are in the retracted configuration, the cutting elements 242 are generally aligned with the upper and lower surfaces of the elongated base 240. The cutting elements 242 are in the retracted configuration when the cutting assembly 233 is extended from the insertion apparatus 230.

To maximize the cutting capabilities of the undercutting system 210, the cutting elements 242 should be formed with a width that is as wide as possible that can fit into the insertion apparatus 210. In certain embodiments, the cutting elements 242 have a width that is between about 5 millimeters and about 10 millimeters.

The cutting elements 242 each comprise a distal end 250 and a proximal end 252. The proximal ends 252 of the cutting elements 242 are all oriented towards the distal end of the cutting assembly 233. Using this configuration causes the cutting elements 242 to be in the retracted position as the cutting assembly 233 is extended from the insertion apparatus 230. The cutting elements 242 pivot to the extended position as the cutting assembly 233 is retracted into the insertion apparatus 230.

The distal end 250 may be provided with a sharpened cutting surface to facilitate the distal end 250 cutting through tissue between the ilium 14 and the sacrum 16. The sharpened surface can also be sufficiently sharp to cut into the ilium 14 and the sacrum 16 and thereby facilitate producing bleeding bone.

As an alternative to or in addition to sharpening the cutting elements 242, an abrasive surface may be provided on at least a portion of the outer surface of the cutting elements 242. Examples of the abrasive surface include chemical etching and sintering material such as beads on the cutting elements 242. Alternatively or additionally, the cutting elements 242 may have a plurality of bristles extending therefrom. Alternatively or additionally, a plurality of teeth may extend from one of the surfaces of the elongated base 240 to provide the cutting action.

As an alternative to forming the cutting elements 242 separate from the elongated base 240, the cutting elements 242 may be integrally formed with the elongated base 240. In this configuration, the cutting elements 242 should have sufficient flexibility to move from the retracted position to the extended position.

The proximal end 252 is used for operably attaching the cutting element 242 to the elongated base 240. To reduce the overall thickness of the cutting assembly 233, the pivoting mechanism 244 may be mounted on a side of the elongated base 240 that is opposite the side on which the distal end is located.

To maximize the cutting ability of the cutting assembly 233, the adjacent cutting elements 242 are mounted in an alternating relationship on opposite sides of the elongated base 240. The distal end 250 of one of the cutting elements 242 may be located proximate to the proximal end 252 of the adjacent cutting element 242.

Because of the configuration in which the cutting elements 242 are attached to the elongated base 240, it is necessary for portions of each cutting element 242 to be on both edges of the elongated base 240. To minimize the potential of tissue snagging on the tissue on the portions of the cutting elements 242 that extend between the opposite sides of the elongated base 240, notches may be formed along the edges of the elongated base 240. In certain embodiments, the cutting elements 242 have a width that is not greater than the width of the elongated base 240.

During the process of cutting tissue using this embodiment of the undercutting system, the cutting assembly 233 is extended and then retracted to a position that is substantially within the insertion apparatus. It is not required that the cutting assembly 233 be completely retracted into the insertion apparatus. Rather, a portion of the cutting assembly 233 that extends from the insertion apparatus does not interfere with the rotation of the undercutting system. The undercutting system is rotated and the extension and retraction process is repeated.

A person of skill in the art will appreciate that the size of the prepared region can be increased by reducing the angle at which the undercutting system 210 is rotated between extensions. The desire to prepare a region having a larger area needs to be balanced with the additional time that is needed for each of the extensions.

In certain embodiments, the cutting elements 242 each have a width of about 3.5 millimeters. In an undercutting process, the cutting assembly 233 is extended between the ilium 14 and the sacrum 16 twelve times where between each of the extensions, the undercutting system 210 is rotated about 30 degrees, as illustrated in FIG. 23.

Depending on factors such as the location of the aperture and the size of the patient, the cutting assembly 233 can be extended up to about 80 millimeters. In other embodiments, the cutting assembly 233 is extended about 60 millimeters. Using this process enables an oblong region between the ilium and the sacrum to be prepared, as illustrated in FIG. 23.

In other embodiments, the cutting elements 242 each have a width of about 7.0 millimeters. In an undercutting process, the cutting assembly 233 is extended between the ilium 14 and the sacrum 16 twelve times where between each of the extensions, the undercutting system 210 is rotated about 30 degrees.

The length at which the cutting assembly 233 is extended can be selected based upon factors such as the distance of an edge of the ilium 14 and the sacrum 16 from the aperture in the ilium 14. The distance that the cutting assembly 233 is extended should be greater than the diameter of the region that is desired to be prepared.

It is possible to monitor the distance in which the cutting assembly 236 is extended using a component that is included in the undercutting system 210. Alternatively or additionally, it is possible to monitor the distance that the cutting assembly 236 has been extended using an imaging technique such as fluoroscopy.

As an alternative to preparing the region between the ilium and sacrum for fusion using a single aperture and extension of the cutting assembly in different directions, as illustrated in FIG. 23, it is possible to use a second aperture. In this configuration, the cutting assembly is inserted through the first aperture in an orientation that is towards the second aperture.

Once the distal end of the cutting assembly is proximate the second aperture, the distal end of the cutting assembly is retrieved through the second aperture. To facilitate guiding the cutting assembly from the first aperture to the second aperture, a probe may be provided on the distal end of the cutting assembly. The probe may have a different shape and/or size to facilitate efficiently directing the cutting assembly from the first aperture to the second aperture.

A reciprocating motion can then be used to cut tissue that is located between the first aperture and the second aperture and between the ilium and the sacrum. Proximate the first aperture and the second aperture, a guide such as a roller may be provided to reduce the tendency of the cutting assembly to cut into the bone adjacent to the first aperture and the second aperture as the cutting assembly transitions from an orientation that is generally transverse to the surface of the bone to generally perpendicular to the surface of the bone.

During the cutting process, the insertion apparatus may be raised or lowered to facilitate preparing not only the region between the ilium and the sacrum but also to cause bleeding bone to be produced on at least a portion of the ilium and the sacrum.

Figure 24:
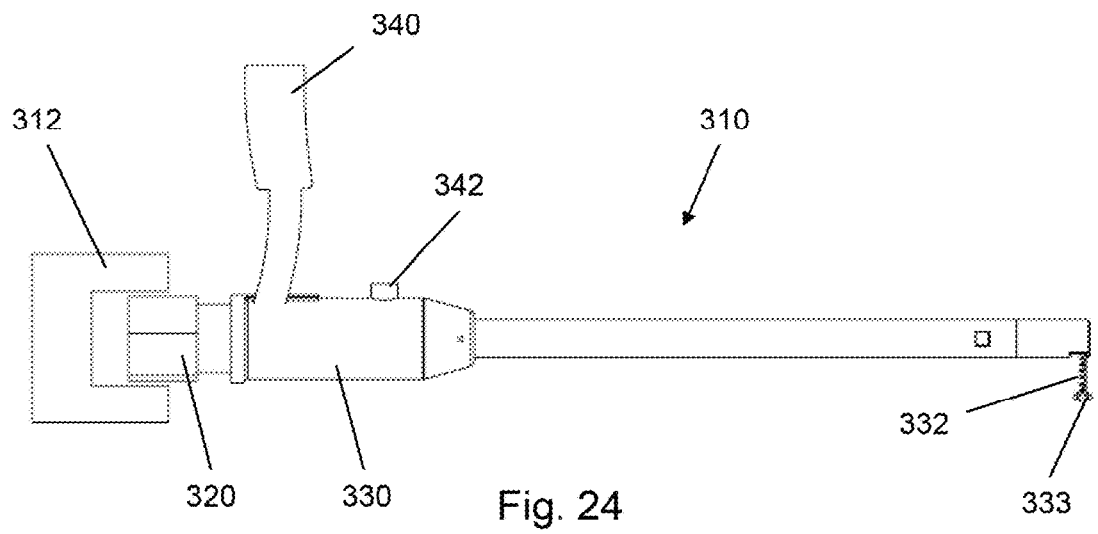
FIG. 24 is a side view of a power device used in conjunction with the insertion apparatus to cause extension and retraction of the probe assembly and/or the cutting assembly.

In another embodiment, the undercutting system 310 is rotated using a powered device 312, as illustrated in FIG. 24. In certain embodiments, the powered device 312 is a power drill. The power drill may be operable using a variety of mechanisms. Examples of these power mechanisms include electricity, battery, pneumatic and hydraulic.

In this embodiment, the proximal end of the undercutting system 310 includes an engagement mechanism that is used for operably attaching the powered device 312 to the undercutting system 310. In certain embodiments, a first portion of the engagement mechanism 320 on the undercutting system 310 has a shape that is generally complementary to a second portion of the engagement mechanism on the powered device 312. In certain embodiments, the first portion 320 is an extension that has a generally hexagonal shape and the second portion is a recess having a generally hexagonal shape.

The first portion 320 may be operably attached to a proximal end of the probe assembly 332 and/or a proximal end of the cutting assembly 333. Using such a configuration enables the probe assembly 332 and/or the cutting assembly 333 to rotate while enabling an outer shaft 340 to remain in a substantially stationary configuration with respect to the patient during the rotation process.

The rotation of the undercutting system 310 may be done at a relatively slow speed. Rotating the undercutting system 310 at a relatively slow speed enhances the ability to control cutting of the ilium, the sacrum and the tissue between the ilium and the sacrum.

In certain embodiments, the rotation is at a speed of between about 15 and about 120 revolutions per minute. In other embodiments, the rotation is at a speed of between about 15 and 30 revolutions per minute.

To enhance the ability to control the undercutting process, the outer portion of the undercutting system 310 may be held to retain the outer portion of the undercutting system 310 in a stationary configuration with respect to the patient. In certain embodiments, a person may manually hold the outer portion of the undercutting system 310. In other embodiments, a handle 340 may be attached to the outer portion of the undercutting system 310 to thereby enhance the ability of the person to hold the outer portion of the undercutting system 310.

The handle 340 may be oriented substantially transverse to the orientation of the insertion apparatus. The handle 340 may have a length that is greater than the width of a typical user's hand. The handle 340 may have a generally cylindrical shape with a diameter of between about ½ of an inch and about 1 inch to facilitate the person's hand extending around the handle 340.

In certain embodiments, the rotation of the engagement mechanism 320 relative to the handle 340 may cause the probe assembly 332 and/or the cutting assembly 333 to be deployed from the insertion apparatus 330. The rate of deployment may be between about 0.05 to about 0.25 millimeters per revolution.

Control of the rotational rate may be done by varying the rate at which the power device 312 is rotated. Alternatively or additionally, the undercutting system 310 may include a gear assembly that enables different rotation rates to be obtained.

Rotation of the powered device 312 in a first direction causes the probe assembly 332 and/or the cutting assembly 333 to be extended from the insertion apparatus 330. Rotation of the powered device 312 in a second direction, which is opposite the first direction, causes the probe assembly 332 and/or the cutting assembly 333 to the retracted into the insertion apparatus 330.

The undercutting system 310 may also include a manual release mechanism 342 that enables the probe assembly 332 and/or the cutting assembly 333 to be manually retracted. While it is also possible for the manual release mechanism 342 to be used to manually extend the probe assembly 332 and/or the cutting assembly 333, the manual extension of the probe assembly 332 and/or the cutting assembly 333 may not provide the same level of control as the use of the powered device 312.

In certain embodiments, brushes could be incorporate into the various configurations of the cutting assemblies described herein. An advantage of using the brushes is that the brushes can cut tissue as well as collect cut tissue to thereby facilitate removal of the cut tissue from the prepared region between the ilium and the sacrum.

Instead of or in addition to relying on flexibility of the probe assembly and/or the cutting assembly to track the joint between the sacrum and the ilium, it is possible to utilize a portion of the insertion apparatus to guide the probe assembly and/or the cutting assembly in a desired direction.

In such an embodiment, an angle at which the probe assembly and/or the cutting assembly is adjusted by changing a portion of the end cap at the distal end of the insertion apparatus. In such a configuration, at least a portion of the end cap is operably attached to the other portions of the insertion apparatus.

Using this configuration reduces the accuracy that must be used with selecting the location at which the aperture is to be drilled in the ilium because in the other embodiments, it was desired for the location of the aperture to be positioned and oriented substantially perpendicular to the adjacent surfaces of the sacrum and the ilium.

Additionally, using this configuration reduces the amount of bending of the probe assembly and/or the cutting assembly as these components exit from the insertion apparatus so that the probe assembly and/or the cutting assembly are generally aligned with the adjacent surfaces of the ilium and the sacrum.

Figure 25:
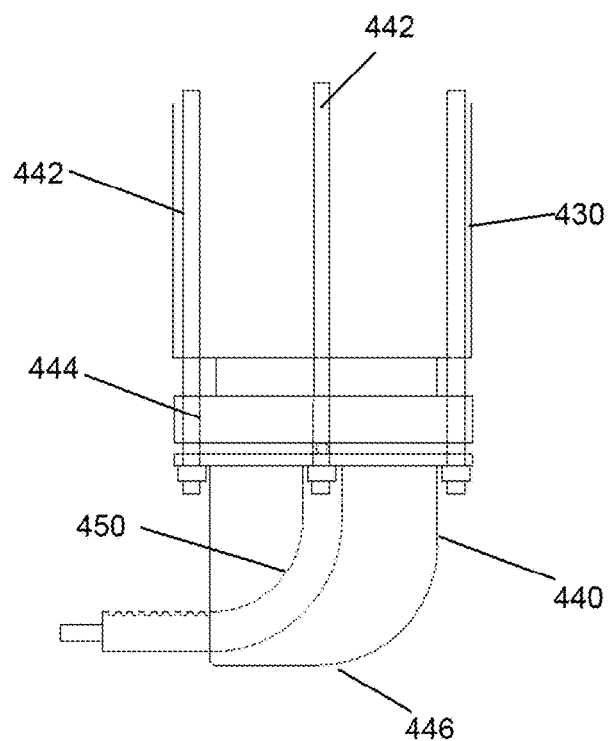
FIG. 25 is a side view of an alternative embodiment of a distal end of the insertion apparatus.

In one such configuration, the end cap 440 is operably attached to the insertion apparatus 430 using a plurality of control arms 442, as illustrated in FIG. 25. A benefit of using this configuration is that the guide assembly and/or the cutting assembly will be more closely aligned with the region between the ilium and the sacrum. As such, the guide assembly and/or the cutting assembly can be more rigid. Using this more rigid configuration reduces the potential of damage to the guide assembly and/or the cutting assembly during the cutting process.

The control arms 442 may be positioned in a spaced-apart configuration proximate an outer surface of the insertion apparatus 430. In certain embodiments, a spacing between each of the control arms 442 is approximately equal.

In one such configuration, there are four control arms 442 that operably attach the end cap 440 to the insertion apparatus 430. Each of the control arms 442 is mounted for movement with respect to the insertion apparatus 430. In certain embodiments, the control arms 442 are slidable with respect to the insertion apparatus 430.

In other embodiments, at least a portion of each of the control arms 442 has a threaded surface. Using the threaded surface enables rotation of the control arm 442 to cause the control arm 442 to move towards or away from the distal end of the insertion apparatus 430 to thereby change the orientation of the end cap 440 with respect to the insertion apparatus 430.

To facilitate pivoting of the end cap 440 with respect to the insertion apparatus 430 in all directions, the end cap 440 may be mounted in a spaced-apart configuration with respect to the distal end of the insertion apparatus 430.

In certain embodiments, the end cap 440 can pivot with respect to the insertion apparatus 430 between about 5 degrees and about 30 degrees. In other embodiments, the end cap 440 can pivot at least about 20 degrees with respect to the insertion apparatus 430.

In this configuration, the end cap 440 may include a plate portion 444 and a cutter direction portion 446. The plate portion 444 may be used for operably attaching the end cap 440 to the control arms 442. In one such configuration, the plate portion 444 may have an aperture extending therethrough proximate to where the control arm 442 to be attached to the plate portion 444.

The cutter direction portion 446 may be attached to the plate portion 444 on a side thereof that is opposite the insertion apparatus 430. An end of the cutter direction portion 446 that is opposite the plate portion 444 may be configured to extend into the sacrum. Using such a process may enhance the ability to retain the distal end of the undercutting system in a desired position during the undercutting process.

In one configuration, the distal end of the cutter direction portion 446 may be curved, as illustrated in FIG. 25. In another configuration, the distal end of the cutter direction portion 446 may be pointed. Providing the distal end of the cutter direction portion 446 with a pointed configuration may enhance the ability of the cutter direction portion 446 to engage the sacrum.

The cutter direction portion 446 has a channel 450 that extends therethrough similar to the embodiment illustrated in FIGS. 1-5. The channel 450 includes a proximal end that is generally aligned with a central axis of the insertion apparatus.

The channel 450 includes a distal end that is oriented at an angle with respect to the proximal end. In certain embodiments, the angle is between about 45 degrees and about 110 degrees. In other embodiments, the angle is between about 60 degrees and about 90 degrees.

Intermediate the proximal end and the distal end, the channel 450 includes a transition region that causes the probe assembly 432 and/or the cutting assembly 433 to deflect from the orientation at the proximal end to the orientation at the distal end.

While it is illustrated that the distal end of the channel 450 extends through a side surface of the cutter direction portion, it is possible for the distal end of the channel 450 to extend through a lower surface of the cutter direction portion 446 or to extend through both the side surface and the lower surface of the cutter direction portion 446.

The distal end of each control arm 442 may be attached to the end cap 440 using a variety of mechanisms that facilitate retaining the control arm 442 in engagement with the end cap 440 while permitting the end cap 440 to pivot with respect to the end cap. An example of one suitable mechanism for attaching the control arm 442 to the end cap 440 is a screw. In certain embodiments, the screw may be recessed in the end cap 440.

Sliding or rotation of the control arms 442 may be controlled using a control mechanism that is mounted proximate the proximal end of the insertion apparatus 430. Providing the control mechanism proximate the proximal end of the insertion apparatus 430 minimizes the size of the incision that needs to be made in the patient and the aperture that needs to be drilled in the bone to provide access to the region between the bones that is to be prepared with the undercutting system.

In certain embodiments, the control mechanism facilitates manual pushing or pulling of the control arms 442. Each of the control arms 442 may include a configuration proximate a proximal end thereof to facilitate gripping by a person desiring to change the position of the control arm 442. In one such configuration, a handle is provides on each of the control arms 442.

Alternatively or additionally, a mechanical assist may be used to control movement of the control arms 442. An example of one such mechanical assist is a servo motor. Other possible configurations for the mechanical assist include pneumatic and hydraulic.

In another embodiment, three control arms 442 operably attach the end cap 440 to the insertion apparatus 430. The control arms 442 may be mounted in a spaced-apart configuration so that a spacing between adjacent control arms 442 is approximately equal.

In another embodiment, a hinge mechanism is provided along a first edge of the end cap to pivotally attach the end cap to the hinge mechanism. An edge of the end cap that is opposite the hinge mechanism is operably attached to at least one control arm. Similar to the control arms discussed above, the control arm causes the end cap to pivot with respect to the insertion apparatus.

Operably attaching the end cap to the insertion apparatus using the control arms enables a direction at which the probe assembly and/or the cutting assembly extends from the undercutting system to be in a direction that generally conforms to an orientation of the surfaces of the ilium and the sacrum.

As such, an element associated with using this configuration of the undercutting system utilizes imaging to assist in setting the orientation of the end cap 440. In one such configuration, a fluoroscope is used for at least one orientation to evaluate the orientation of the ilium and the sacrum proximate to where the undercutting system is to be used.

In another configuration, the end cap 540 is movably mounted with respect to the distal end of the insertion apparatus 530, as illustrated in FIGS. 26 and 27. In this configuration a flexible material is used to operably mount the end cap 540 with respect to the insertion apparatus 530.

Using this configuration allows the end cap 540 to pivot with respect to the insertion apparatus 530 during the process of using the probe assembly and/or the cutting assembly to prepare the region between the ilium and the sacrum for the sacroiliac fusion. By pivoting the end cap 540, the bending of the portion of the probe assembly and/or the cutting assembly that extends beyond the end cap 540 is reduced.

A distance between the insertion apparatus 530 and the end cap 540 may affect the angle at which the end cap 540 is pivotable with respect to the insertion apparatus 530. Similarly, the resilient material that is used to operably attach the end cap 540 to the insertion apparatus 530 can also affect not only the angle at which the end cap 540 is pivotable with respect to the insertion apparatus 530 but also the ease at which the end cap 540 pivots with respect to the insertion apparatus 530.

As an alternative to using the resilient material to attach the end cap 540 to the insertion apparatus, it is possible to use other mechanisms. An example of one such alternative attachment mechanism is a hinge.

The end cap 540 includes a channel 550 extending therethrough that causes the probe assembly and/or the cutting assembly to be deflected from an initial configuration that is generally parallel to the axis of the insertion apparatus 530 to a configuration that is generally perpendicular to the axis of the insertion apparatus 530 as the probe assembly and/or the cutting assembly emerges from the end cap 540.

The channel 550 may be formed with a width and a height that are both greater than the width and the height of the probe assembly and the cutting assembly. Using such a configuration enables the end cap 540 to pivot with respect to the insertion apparatus 530 without the contact of the probe assembly or cutting assembly against the side of the channel 550 restricting the pivoting of the end cap 540.

Another configuration of the undercutting system enables pivoting of the end cap 640 with respect to the insertion apparatus 630, as illustrated in FIGS. 28 and 29. At least a portion 660 of the distal end of the insertion apparatus 630 may have a semi-circular configuration to enhance the ability of the end cap 640 to pivot with respect to the insertion apparatus 630.

The end cap 640 may have a recess 662 formed therein that is adapted to receive the portion 660 of the distal end of the insertion apparatus 630. At least part of the recess 662 may have a semi-circular configuration to enhance the ability of the end cap 640 the pivot with respect to the insertion apparatus 630.

The channel 650 extends through the distal end of the insertion apparatus 630. The channel 650 may be formed with a height and a width that are both greater than the height and the width of the probe assembly and the cutting assembly to facilitate pivoting of the end cap 640 with respect to the insertion apparatus 630. Similarly, the channel 650 in the end cap 640 may also be formed with greater dimensions to facilitate pivoting of the end cap 640 with respect to the insertion apparatus 630.

A retaining pin 670 may be used to prevent the end cap 640 from becoming disengaged from the insertion apparatus 630. The retaining pin 670 may extend across the end cap 640 as illustrated in FIG. 28. A groove 672 may be formed in the insertion apparatus 630 proximate the distal end thereof. The groove 672 may extend substantially around the outer surface of the insertion apparatus 630. The groove 672 receives the retaining pin 670 to thereby retain the end cap 640 in pivotal engagement with the insertion apparatus 630.

A few of the challenges associated with preparing bleeding bone surfaces on the ilium and the sacrum include providing the probe assembly and/or the cutting assembly that is deflectable from an initial configuration inside of the insertion apparatus to an extended configuration between the ilium and the sacrum while at the same time the probe assembly and/or the cutting assembly have sufficient structural rigidity to cut through tissue between the ilium and the sacrum as the probe assembly and/or the cutting assembly is progressively extended from the insertion apparatus into the space between the ilium and the sacrum so that a progressively larger area can be prepared.

Additional challenges associated with preparing the bleeding bone surfaces on the ilium and the sacrum result from the fact that the surfaces of the ilium and the sacrum are not substantially flat and a distance between the ilium and the sacrum does not remain consistent.

Another embodiment of the cutting assembly, which is illustrated in FIGS. 30-33, seeks to overcome these issues. The cutting assembly 733 includes an outer cutting portion 740 and an inner expansion portion 742.

The outer cutting portion 740 includes a relatively thin distal end 750. While the distal end 750 may have a thickness that is less than the thickness of the other portions of the cutting assembly 733, it does not have to be very sharp. Such a configuration facilitate defining the joint line between the ilium and the sacrum as the cutting assembly 733 is extended from the insertion apparatus while minimizing the cutting assembly 733 cutting too deeply into the ilium or the sacrum.

Cutting too deeply into the ilium or the sacrum is undesirable because the ilium and the sacrum are considerably harder than the tissue that is between the ilium and the sacrum. Greater force is thereby needed to cut into the ilium or the sacrum than is needed to cut the tissue between the ilium and the sacrum.

Such additional force requires the components of the undercutting system to be stronger than if the undercutting system is intended to cut through the tissue between the ilium and the sacrum as well as to disturb the surfaces of the ilium and the sacrum to produce bleeding bone. The additional force needed to cut through the ilium or the sacrum also presents challenges in providing such force through the insertion apparatus, which has a relatively thin diameter.

The outer cutting portion 740 may include an upper cutting portion leg and a lower cutting portion leg. Each of the cutting portion legs may include a flexible base 754 to which a plurality of cutting elements 752 is mounted.

The flexible base 754 enables the outer cutting portion 740 to deform from the initial configuration (FIG. 30) to the expanded configuration (FIG. 33). A variety of materials may be used to fabricate the flexible base 754 as long as such materials are suited for use in medical applications.

The cutting elements 752 include a sharpened surface along at least one side edge thereof. In certain embodiments, the sharpened surfaces are provided on both side edges of each cutting element 752 so that the cutting assembly 733 is capable of cutting tissues when rotated in both directions.

In other embodiments, one of the side edges has a sharper surface and the opposite side edge. In certain embodiments, the cutting elements 752 are fabricated from a metallic material such as stainless steel, which is suited for use in medical applications.

In still other embodiments, the cutting elements 752 may include an abrasive outer surface. This abrasive outer surface may be in addition to or as an alternative to the sharpened surfaces. Alternatively or additionally, the cutting elements 752 may have a plurality of bristles extending therefrom.

The inner expansion portion 742 is positioned between the upper cutting portion leg and the lower cutting portion leg. In certain embodiments, the inner expansion portion 742 extends substantially to the distal end of the cutting assembly 733.

The inner expansion portion 742 may be formed with a width that is less than the width of the outer cutting portion 740. In other embodiments, the inner expansion portion 742 has a width that is approximately the same as the width of the outer cutting portion 740.

The inner expansion portion 742 may be fabricated from a flexible material. A person of skill in the art will appreciate that the flexible material needs to be sufficiently strong to cause the inner expansion portion 742 to expand from the retracted position to the expanded position while resisting damage from contact with the outer cutting portion 740 as well as contact with the ilium, the sacrum and the tissue that is between the ilium and the sacrum. In certain embodiments, the inner expansion portion 742 is fabricated from a polymeric material.

The inner expansion portion 742 may be moved between the retracted position and the expanded position by placing an object therein. One criteria in selecting the material that is placed in the inner expansion portion 742 is the ability to readily insert and remove the object from the inner expansion portion 742.

In certain embodiments, the object placed in the inner expansion portion 742 is a gas such as air. In other embodiments, the object placed in the inner expansion portion 742 is a liquid such as water. In still other embodiments, the object placed in the inner expansion portion 742 is a solid such as beads. In other embodiments, the object placed in the inner expansion portion is a series of strips that are inserted in a sequential manner to gradually increase the thickness. In a situation, where the object is the series of strips, it may not be necessary for the inner expansion portion 742 to be used.

While it is intended that the object placed in the inner expansion portion 742 is to remain inside of the inner expansion portion 742 and not contact the patient, it is possible that the object may contact the patient. Accordingly, the object should be selected to not cause any negative interactions if the object comes into contact with either the skin on the surface of the patient or tissue inside of the patient proximate to where the undercutting system is being used.

When the cutting assembly 733 is in the insertion apparatus and then initially extended from the insertion apparatus, the inner expansion portion 742 is in a relatively flat configuration, as illustrated in FIG. 30.

Thereafter, the inner expansion portion 742 is progressively increased in size as illustrated in FIGS. 31-33. This process enables a progressively thicker region to be prepared between the ilium and the sacrum.

In certain embodiments, the increasing the size of the inner expansion portion 742 is gradually done as the cutting assembly 733 is rotated. In other embodiments, the inner expansion portion 742 is periodically increased in size such as after each rotation of the cutting assembly 733.

Initially, the outer cutting portion 740 cuts the tissue between the ilium and the sacrum. The flexible nature of the outer cutting portion 740 and the inner expansion portion 742 facilitates the cutting assembly following the surfaces of the ilium and the sacrum as well as accommodates for differences in the distance between the ilium and the sacrum.

Once the inner expansion portion 742 is in the expanded position, which is illustrated in FIG. 33, the upper cutting portion leg and the lower cutting portion leg are sufficiently urged against the surfaces of the ilium and the sacrum to disrupt such surfaces and cause bleeding bone on these surfaces. As described above, the bleeding bone is an important aspect in providing sacroiliac fusion.

After the cutting process is complete, the object is removed from the inner expansion portion 742 so that the outer cutting portion 740 may return to the initial collapsed configuration where the upper cutting portion leg is proximate the lower cutting portion leg as illustrated in FIG. 30. At such time, the cutting assembly 733 is withdrawn from between the ilium and the sacrum.

While the concepts of the invention are primarily described in conjunction with preparation for a sacroiliac fusion, a person of skill in the art will appreciate that the concepts may be adapted for other joints in the body. The concepts may also be used for preparing an interior region of a bone.

In the preceding detailed description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting.

It is to be understood that other embodiments may be utilized and structural or logical changes may be made without departing from the scope of the present invention. The preceding detailed description, therefore, is not to be taken in a limiting sense, and the scope of the present invention is defined by the appended claims.

It is contemplated that features disclosed in this application, as well as those described in the above applications incorporated by reference, can be mixed and matched to suit particular circumstances. Various other modifications and changes will be apparent to those of ordinary skill.

The invention claimed is:

1. A method of preparing a region between adjacent bones for fusion, wherein the method comprises:
    forming a first aperture that extends through one of the bones;
    inserting an undercutting system into the first aperture, wherein the undercutting system comprises an insertion apparatus and a cutting assembly; and
    cutting a first path between the adjacent bones by extending or retracting the cutting assembly with respect to the insertion apparatus;
    at least partially retracting the cutting assembly;
    turning the insertion apparatus with respect to the bone having the aperture formed therein;
    cutting a second path between the adjacent bones by extending or retracing the cutting assembly with respect to the insertion apparatus; and
    retracting the cutting assembly to substantially within the insertion apparatus.

2. The method of claim 1, wherein cutting the first path and the second path is accomplished by at least one of a sharpened surface on the cutting assembly, an abrasive surface on the cutting assembly or a plurality of bristles extending from the cutting assembly.

3. The method of claim 1, and further comprising:
    forming a second aperture that extends through one of the bones; and
    extending a distal end of the cutting assembly through the second aperture.

4. The method of claim 1, wherein extending or retracting the cutting assembly comprises sliding the cutting assembly with respect to the insertion apparatus and wherein the aperture is oriented at an angle of between 45 degrees and 90 degrees with respect to a surface of the bone through which the aperture extends.

5. The method of claim 1, and further comprising changing an orientation of a portion of the insertion apparatus from which the cutting assembly extends or changing a thickness of at least a portion of the cutting assembly.

6. The method of claim 1, and further comprising:
    using an imaging technique to determine an orientation of the bone proximate the aperture; and
    changing an orientation of a portion of the insertion apparatus from which the cutting assembly extends based upon the orientation of the bone proximate the aperture.

* * * * *